(12) United States Patent
Hochman et al.

(10) Patent No.: US 6,786,885 B2
(45) Date of Patent: *Sep. 7, 2004

(54) PRESSURE/FORCE COMPUTER CONTROLLED DRUG DELIVERY SYSTEM WITH EXIT PRESSURE CONTROL

(75) Inventors: Mark Hochman, Lake Success, NY (US); Claudia Hochman, Lake Success, NY (US); Angelo Ascione, Woodbridge, NJ (US); Lawrence Brown, Enola, PA (US); Hardie Johnson, Enola, PA (US); Michelle Lockwood, Mechanicsburg, PA (US)

(73) Assignee: Milestone Scientific Inc, Livingston, NJ (US)

( * ) Notice: Subject to any disclaimer, the term of this patent is extended or adjusted under 35 U.S.C. 154(b) by 521 days.

This patent is subject to a terminal disclaimer.

(21) Appl. No.: 09/766,772

(22) Filed: Jan. 22, 2001

(65) Prior Publication Data

US 2002/0016567 A1 Feb. 7, 2002

Related U.S. Application Data

(62) Division of application No. 09/201,464, filed on Nov. 30, 1998, now Pat. No. 6,200,289.
(60) Provisional application No. 60/081,388, filed on Apr. 10, 1998.

(51) Int. Cl.[7] .............................................. A61M 31/00
(52) U.S. Cl. ................. 604/67; 128/DIG. 12; 604/151
(58) Field of Search ................. 604/65–67, 93.01, 604/118, 181, 183, 131, 151–152, 154–156; 128/DIG. 12, 13; 700/90

(56) References Cited

U.S. PATENT DOCUMENTS

| 1,682,344 A | 8/1928 | Lesieur |
| 3,565,076 A | 2/1971 | Kadan |
| 3,572,319 A | 3/1971 | Bittner et al. |
| 3,623,474 A | 11/1971 | Heilman |
| 4,168,707 A | 9/1979 | Douvas et al. |
| 4,395,258 A | 7/1983 | Wang et al. |
| 4,403,988 A | 9/1983 | Binard et al. |
| 4,533,346 A | 8/1985 | Cosgrove, Jr. et al. |
| 4,710,172 A | 12/1987 | Jacklich et al. |
| 4,731,058 A | 3/1988 | Doan |
| 4,747,824 A | 5/1988 | Spinello |
| 4,988,336 A | 1/1991 | Kohn |
| 5,080,653 A | 1/1992 | Voss et al. |
| 5,180,371 A | 1/1993 | Spinello |
| 5,295,967 A | * 3/1994 | Rondelet et al. ............ 604/154 |
| 5,352,195 A | 10/1994 | McEwen |
| 5,690,618 A | 11/1997 | Smith et al. |
| 6,022,337 A | 2/2000 | Herbst et al. |

OTHER PUBLICATIONS

The Pressures Created by Inferior Alveolar Injections, British Dental J. Vol./ No 144 (May 2, 1978); by J.P. Rood; pp 280–282.

(List continued on next page.)

*Primary Examiner*—Loan H. Thanh
(74) *Attorney, Agent, or Firm*—Gottlieb, Rackman & Reisman, P.C.

(57) ABSTRACT

An automatic injection device includes a drive mechanism and a sensor used to determine an internal characteristic such as a force or internal pressure generated during an injection process. This characteristic is then used as a control parameter by a microprocessor or controller which generates corresponding commands to the drive mechanism. In a particularly advantageous embodiment, the characteristic is used to calculate an exit pressure at which fluid ejected by the device through an elongated tube. The drive mechanism is then operated in such a manner that the exit pressure is maintained at a predetermined level to insure that a patient does not suffer pain and/or tissue damage.

24 Claims, 17 Drawing Sheets

OTHER PUBLICATIONS

Periodontal Ligament Injection—Distribution of Injected Solutions; Oral Surg. Mar. 1983 vol. 55 No 3; by G.N. Smith, R.E. Walton; Dept. of Endodontics Medical College of Georgia School of Dentistry; pp 232–238.

Periodontal Ligament Injection—A Clinical Evaluation; JADA Articles 1981; by R.E. Walton and B.J. Abbott; pp 371–375.

Pressures Created by Dental Injections; Dental Injection Pressures vol 60 No 10; by E.L. Pashley, R. Nelson, and D.H. Pashley Dept of Pedodontics, Oral Biology, and Physiology, Medical College of Georgia, Augusta–Georgia 30912; J. Dent Res—Dental Injection Pressures vol. 60 No 10 Oct. 1981; pp 1742–1748.

Bone and Root Resorption—Effects of the Force Deveolped During Periodontal Ligamnet Injections in Dogs; Oral Surg Oral Med Oral Pathol 1992 vol/no 74; by W–J Pertot and J. Dejou; Universite D'Aix–Marseille III–U.F.R. D'Odontologie, Unite Interface Matrice Estracellulaire Biomate Riaux pp 357–365.

* cited by examiner

Machine Profile Setup Screen
Set Values for Components of Delivery System
Setup Variable for Machine

PRESSURE/FORCE COMPUTER CONTROLLED DRUG DELIVERY SYSTEM WITH EXIT PRESSURE CONTROL

RELATED APPLICATIONS

This application claims priority to U.S. Provisional Application Serial No. 60/081,388 filed Apr. 10, 1998, incorporated herein by reference, and is a continuation of U.S. patent application Ser. No. 09/201,464 filed Nov. 30, 1998, now U.S. Pat. No. 6,200,289.

The present invention relates generally to improvements to the delivery of drugs, particularly to systems for subcutaneous injection/aspiration (syringes) for drug delivery providing intermittent, episodic or limited drug delivery (as opposed to continuous drug delivery of syringe pumps). More specifically, this invention relates to an improved means of subcutaneous drug (fluid) injection and aspiration, providing a means and method of controlling and monitoring the interaction of specific flow rate and pressure during fluid injection and aspiration with a hypodermic hollow-core needle. b. Description of the Prior Art Infusion pumps devices and systems are relatively well known in the medical arts, for use in delivery or dispensing a prescribed medication to a patient. These may be compact pump housings or larger stationary pump housing units. The administration of prescribed drugs has been described in the literature as administration to a patient through infusion tubing and an associated catheter or the like, thereby introducing the drug intravenously. These systems have seen improvements over time with respect to determining infusion line occlusion. Line blockage would cause pressure in the syringe to increase. Systems in the prior art have been developed to identify a predetermined threshold or to monitor pressure to determine means for selecting ranges of occlusion pressures to insure patient safety. U.S. Pat. Nos. 5,295,967; 4,731,058; and 5,080,653 show systems (with syringe pumps or the like) which are adequate for the intended use of intravenous drug delivery and more specifically for monitoring occlusion during infusion. However, these systems do not provide a means for drug delivery subcutaneously via a hypodermic needle. Moreover these systems do not provide a means of aspiration during drug delivery, which is a medical requirement for subcutaneous injection in an attempt to avoid intravascular placement of the hypodermic needle.

Pain, tissue damage and post-op complications have long been tolerated as negative side effects from the use of existing hypodermic drug delivery injection systems. This is well documented in both the dental and medical literature. The pain and tissue damage are as a direct result of uncontrolled flow rate in conjunction with excessive pressures created during the administration of drug solutions within the tissue spaces. Subjective pain response of a patient has been demonstrated to be minimized at specific flow rates during the administration of a drug. Also, it has been scientifically demonstrated that particular pressures (excessive without occlusion, per se) for a specific tissue type will cause damage. It is therefore critical that a specific flow rate in conjunction with a specified pressure range be maintained during the delivery of fluids (drugs) when a subcutaneous injection is given preventing subjective pain response as well as tissue damage. It is also necessary that this system have the capability to aspirate under controlled conditions of rate and pressure to avoid the same negative side effects during fluid movement. U.S. Pat. No. 5,180,371 to Spinello, incorporated herein by reference, presented an invention which allowed a rate to be set for the drug via a hypodermic needle. That invention however did not disclose means of determining, detecting or monitoring pressure during the administration of a drug.

During the early 1980's, several researchers ( See for instance Rood, *The Pressure Created by Inferior Alveolar Injections*, British Dental J. 144:280–282 (1978); Walton and Abbot, *Periodontal Ligament Injection; a Clinical Evaluation* JADA.(Oct. 1981); Smith and Walton, *Periodontal Ligament Injection; Distribution of Injected Solution* Oral Surg 55:232–238 (1983)} clearly demonstrated and concluded that the pressure created by the injected fluid is critical to preventing tissue damage and a pain response. Variability, different collagen types and connective tissue densities results in different tissue compliance and distensibility. These variations are found between subjects and within the individual subjects. Rood in his 1978 article states that "[t]he relationship between rate of injection and pressure rise seen clearly with the smaller volumes was lost when 2.0 ml was injected. Several high pressures were recorded and some unexpected low ones. Many tracings showed a pattern suggestive of tissue disruption and it is possible that said low pressures were due to the fluid no longer being contained within the pterygomandibular space as the volume injected was similar to the previously estimated volume of the tissue space." Hence, it appears that the rate of flow is not directly related to pressure during an interstitial injection.

Smith and Walton described in their article identified supra discussed above that they have performed a histologic animal study (canines) using a technique to calibrate manual pressures produced. They concluded that the "Volume injected and needle location were not always related to distribution . . . Injecting under moderate to strong back pressure gave deeper and more widespread dye penetration." This once again confirms that pressure is the critical variable in the distribution of the solution within tissues and the volume is not always related to the pressure produced.

Pashley, Nelson & Pashley in *"Pressures Created by Dental Injections"* (J Dent Res 1981) used a pressure transducer and fixed flow rate created by a motor driven traditional syringe clearly demonstrated that different tissues have a different tissue compliance. Interstitial pressure variability was statistically and clinically significant even with a fixed flow rate. Therefore, it may be concluded that they produced great variations of pressure by using a metered flow rate.

Pertot and Dejou described in their article *"Effects of the force developed during periodontal ligament injections in dogs"* (Oral Surg. Oral Med, Oral Pathol. 1992) how they used a syringe coupled to a miniature force transducer and found a positive correlation between the number of osteoclasts and the force applied on the syringe plunger, which indicated the pressure generated in the PDL space enhanced osteoclastic activity. This experiment again indicates that pressure is a critical factor to tissue damage and is dependent on the resistance encountered and not the flow rate of the solution into the tissues.

One of the goals of dentistry and medicine should be to administer care to patients in the most humane and painless manner. The sine qua non of any treatment is to produce a desired result without causing damage or pain to the individual. Therefore there is an important need in all fields of surgery for an injection system which can be used to administer a fluid while causing substantially no pain or tissue damage to the patient.

OBJECTIVES AND SUMMARY OF THE INVENTION

The present invention has for its objective to minimize subjective pain response and any potential tissue damage to a patient resulting from of inappropriate pressures produced during the administration of a drug via hypodermic needle.

A further objective is to provide these benefits using a variety of different drug sources, i.e., standard syringes as well as, anesthetic cartridges or carpules.

A further objective is to provide a system which can be used easily by a clinician with very minimal training.

A further objective is to provide a system of the type discussed above having a substantial disposable portion.

A further objective is a system which can provide not only injections but also proper aspiration and/or biopsy with the capability to control both rate and pressure.

A further objective is to provide a system which automatically determines and uses the exit (or entry) pressure as a control parameter for any size and combination of syringe, tube or needle.

Prior art references are known which attempt to utilize a pressure transducer to measure the pressure within the syringe (See for instance U.S. Pat. No. 5,295,967). A major deficiency of these systems is their inability to adjust the flow rate and/or pressure of the fluid to compensate for changes in resistances throughout the system, or to the exit pressure. (Exit pressure refers to the fluid pressure just downstream of the needle tip within the patient's body). Moreover, the prior art references fail to provide any means of determining this exit pressure. The present invention comprises a microprocessor-based system which measures a pressure or force generated externally of the tissues, and then uses this measurement to accurately determine the corresponding exit pressure. In other words, by using specific software, the system monitors the exit pressure and generates and maintains a specific flow rate even when there are changes in the resistance of the system.

The invention also provides a system which automatically compensates for the total resistance encountered within the system and which has been proven to influence flow rates and measured pressure. It is believed that this is the first system which has the capability to provide a precisely defined flow rate and desired pressure by taking into account the total system resistance. It is submitted that without this capability, flow rates and exit pressures cannot be precisely derived for varying disposable assemblies consisting of different syringe, tubing, needle sizes and fluid characteristics. A critical feature of the system is that it controls and monitors the pressure using a transducer that generates a feedback parameter.

Briefly, a system in accordance with this invention for dispensing a fluid by injecting the same into a patient includes a mechanical assembly and an electrical controller. The mechanical assembly consists of a drive mechanism and a disposable portion consisting of a fluid storage device such as a syringe, a carpule and the like, and a fluid delivery section including a tube coupled to said fluid storage device and terminating in a needle adapted to be inserted into the subject tissue. The drive mechanism includes a housing with an internal motor and a mount for mounting the fluid storage device on the housing. The fluid storage device includes a reciprocating plunger. A coupling is used to move the plunger with said motor. Importantly, a transducer is used to sense the force or pressure generated by the motor and applied by the plunger within the fluid storage device. If a carpule is used for the fluid storage device, an adapter is also provided to allow the same mount to secure the carpule as well. The mount is arranged and constructed to secure syringes or carpules having a large variety of sizes. The motor, the coupling associated with the motor and the electronic controller discussed below is at least partially disposed within the housing for protection.

The electrical controller is provided for controlling the overall operation of the system. The controller includes a master microprocessor which may be provided as a standard stand-alone PC or laptop PC, and an internal slave microprocessor operating in response to commands from the master microprocessor. The master microprocessor provides the interfacing with the clinician and collects data regarding the mechanical assembly. The master microprocessor is also associated with a display used to provide instructions to a clinician and an input device, which may be a keyboard, a touch screen or voice-activated device to collect information from the clinician. The master microprocessor is further associated with a memory which holds several data banks, each data bank being associated with one of the elements of the disposable portion as well as other parameters.

The fluid storage device is filled and a setup process is initiated during which various operational parameters are calculated, retrieved or received from the clinician. The clinician also specifies the fluid flow rates and peak exit pressure and a total amount of fluid to be dispensed. Then he operates a pneumatic control such as a foot pedal and initiates the fluid flow. Alternatively, commands may be initiated by the clinician either electronically or by voice commands. During dispensing, the output from the transducer is used to calculate the current exit fluid pressure. If this exit pressure approaches a certain threshold, the fluid flow rate is automatically reduced to prevent excessive exit pressure, thereby ensuring that the patient does not suffer undue pain and no tissue is damaged. Several optional features are also provided including aspiration, purging or charging the media with or without air.

Alternatively, the system may be operated in a biopsy mode in which the entry pressure and the outbound or withdrawn fluid flow rate are the relevant control parameters.

Throughout the process, the clinician is provided with constant current information on the ongoing process, both visual and aurally, including the current flow rate, total volume ejected or aspired, exit or entry pressures and other parameters. The slave microprocessor receives commands from the master microprocessor and generates the drive signals required to operate the motor.

BRIEF DESCRIPTION OF THE DRAWINGS

FIG. 12A shows a typical display showing various possible choices for the elements of the disposable portion;

FIG. 12B shows a typical display summarizing the operational characteristics and parameters of the current procedure;

DETAILED DESCRIPTION OF THE INVENTION

Figure 1:
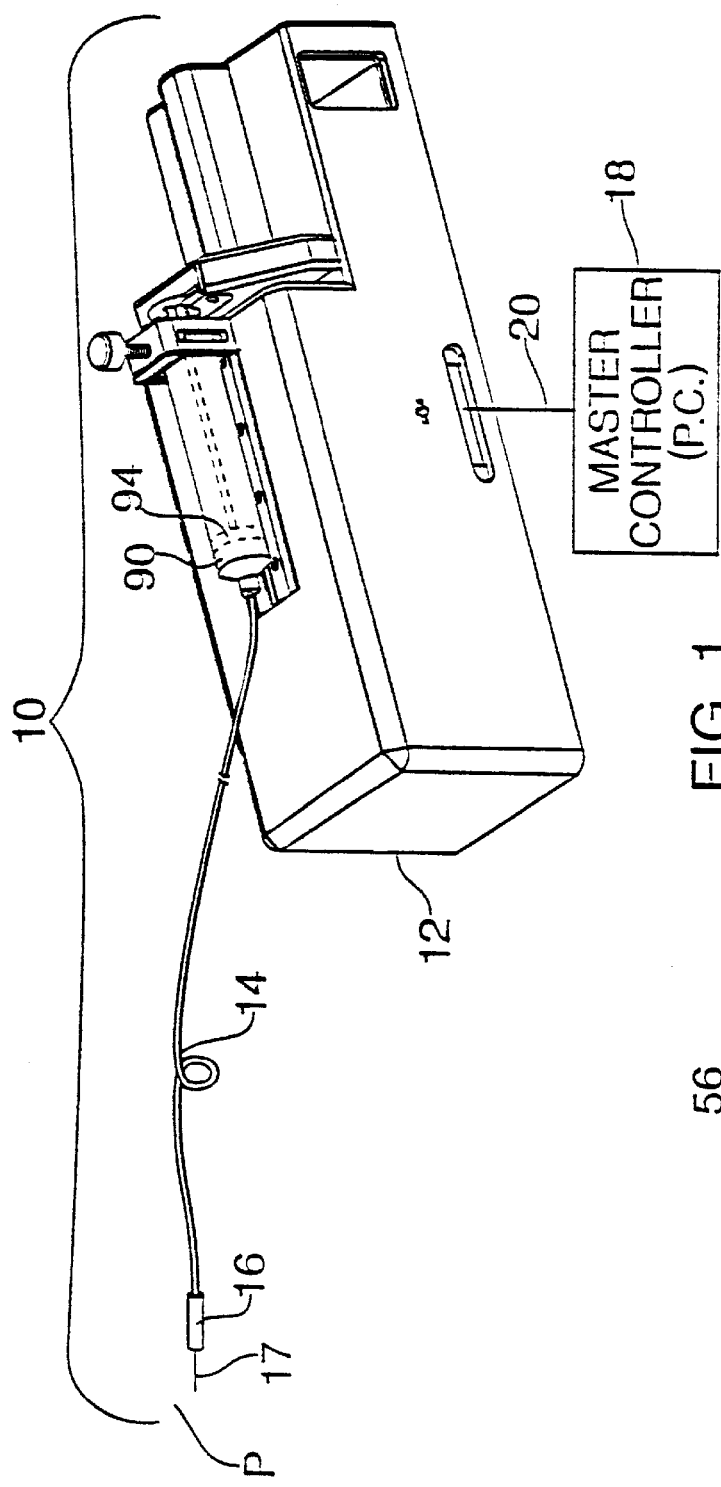
FIG. 1 shows a diagram illustrating the major components of the mechanical system for the present invention.
Figure 7A:
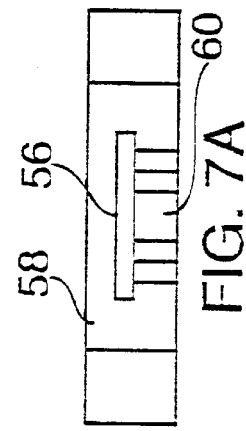
FIG. 7A shows a top view of the platform 30 of FIG. 2.
Figure 7B:
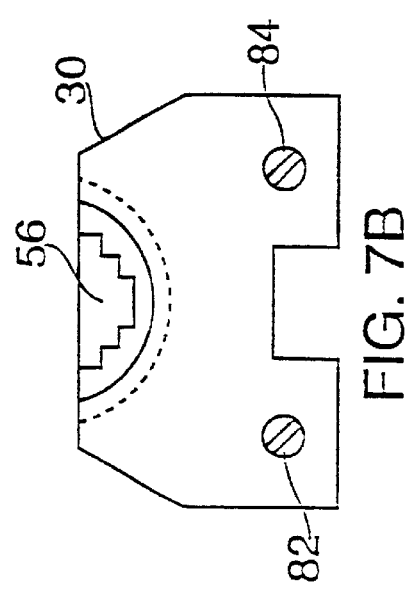
FIG. 7B shows a side elevational view of the platform 30 of FIGS. 2 and 6.
Figure 2:
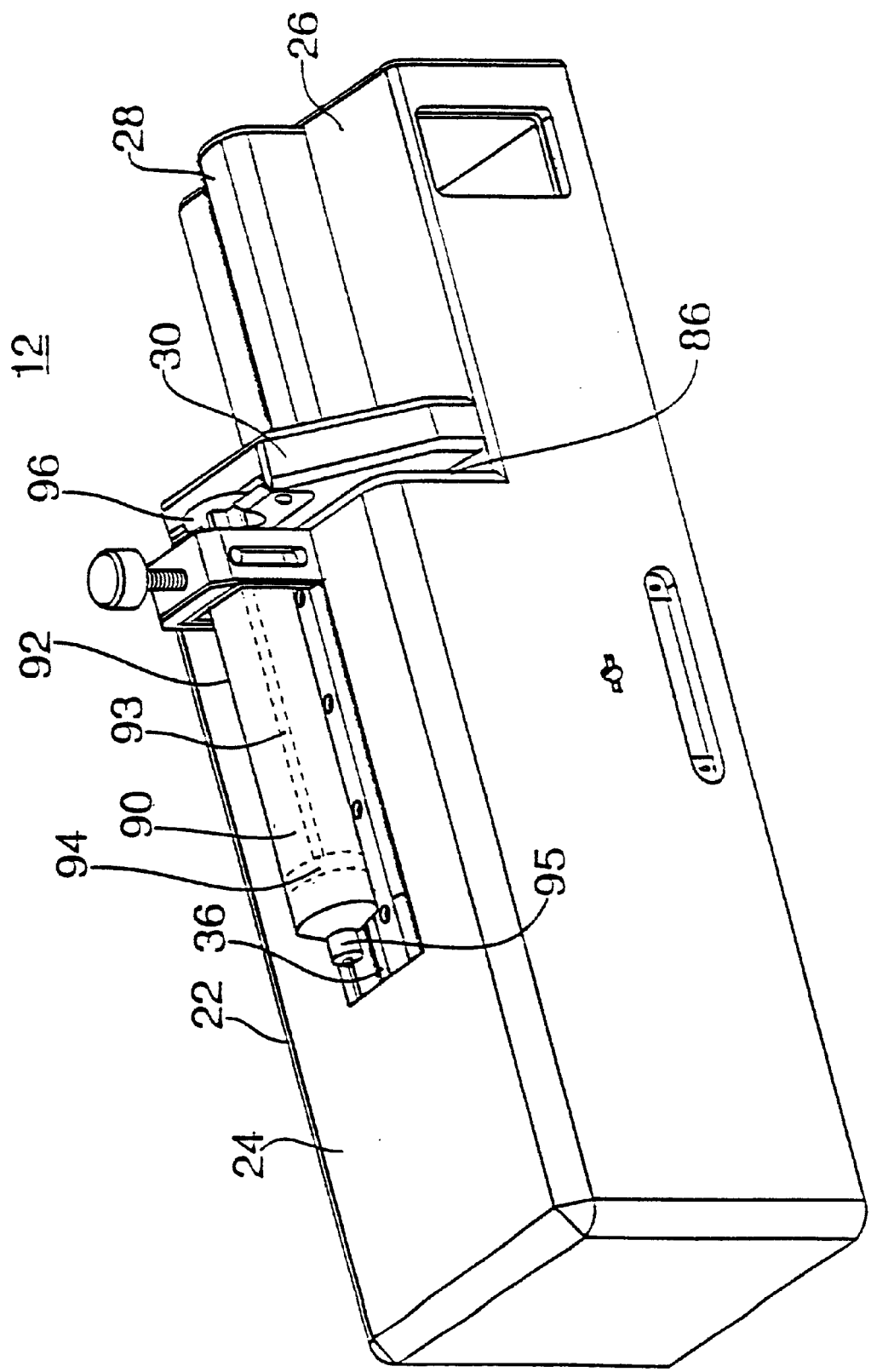
FIG. 2 shows an orthogonal view of the drive mechanism.

The subject invention pertains to a system for delivering drugs such as an anesthetic, or to provide aspiration, for example for a biopsy, in an efficient manner which insures at the same time that pain to the patient is minimized. The system includes a mechanical assembly cooperating with an electronic controller.

The mechanical assembly is illustrated in FIGS. 1–9 and the electronic controller 150 is shown in FIGS. 10–18.

A drug delivery system 10 constructed in accordance with this invention includes drive mechanism 12, a delivery tube 14 and a handle 16 terminating with a needle 17. More particularly, a syringe 90 (or other fluid storage device) is mounted on the drive mechanism with one end of tube 14 being coupled to the syringe 90. The drive mechanism 12 operates a plunger 94 to selectively eject fluid out through the tube 14 handle 16, and needle 17 or alternatively to draw fluid in. The drive mechanism 12 is associated with an external controller for selecting various operational parameters discussed in more detail below. This external controller may be provided on the housing of the drive mechanism or may be provided as a separate control unit 18 coupled to the drive mechanism 12 by a cable 20. The control unit 18 may be for instance a PC or laptop computer. Alternatively, the control unit 18 may be internal.

Details of the drive mechanism 12 are seen in FIGS. 2–5. Starting with FIG. 2, drive mechanism 12 includes a housing 22 with a top surface 24 and intermediate surface 26 disposed below top surface 24. On surface 26 there is formed a rail 28 extending along the longitudinal axis of housing 22. A platform 30 which is disposed on the rail 28 can be reciprocated back and forth in parallel with said longitudinal axis, as described in more detail below.

Figure 5A:
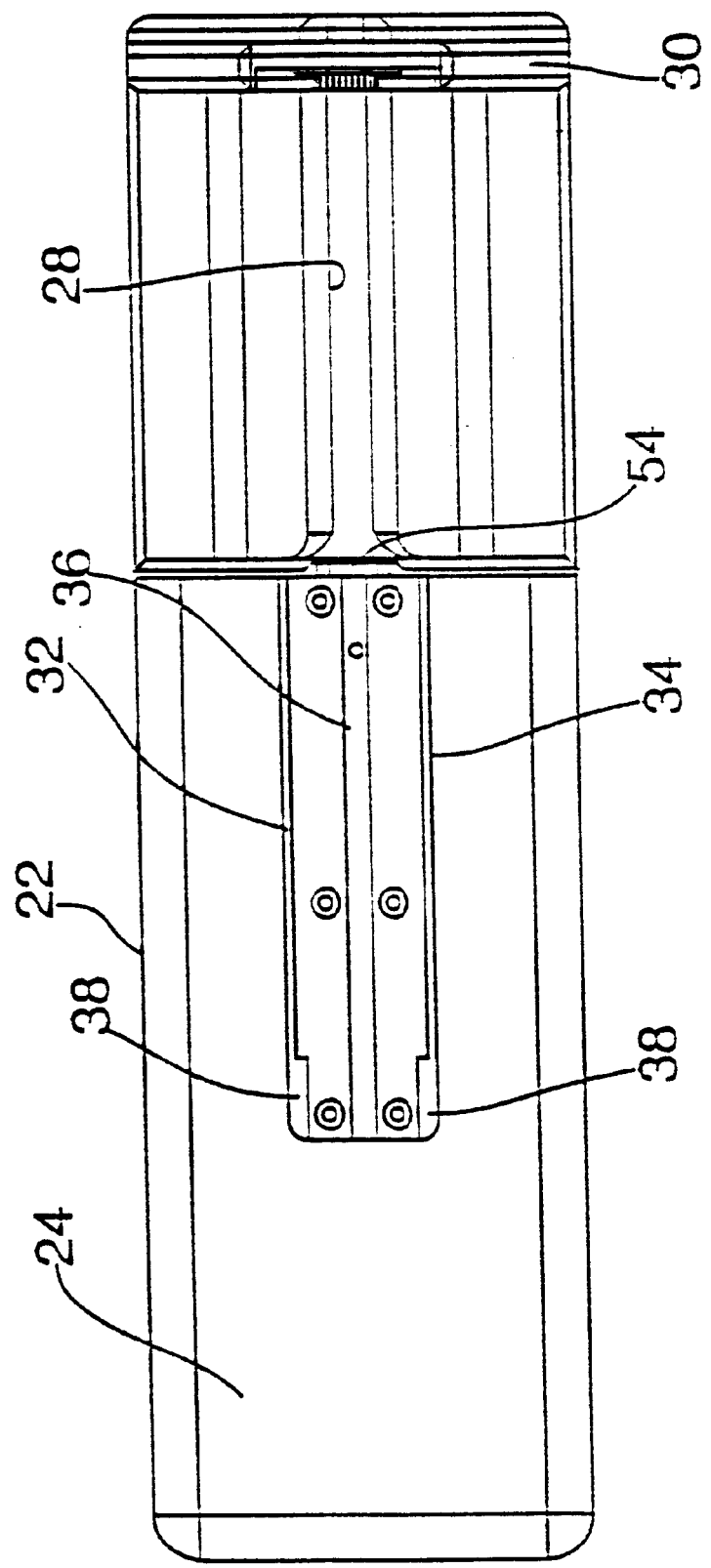
FIG. 5A shows a top view of the housing without the bracket.
Figure 5B:
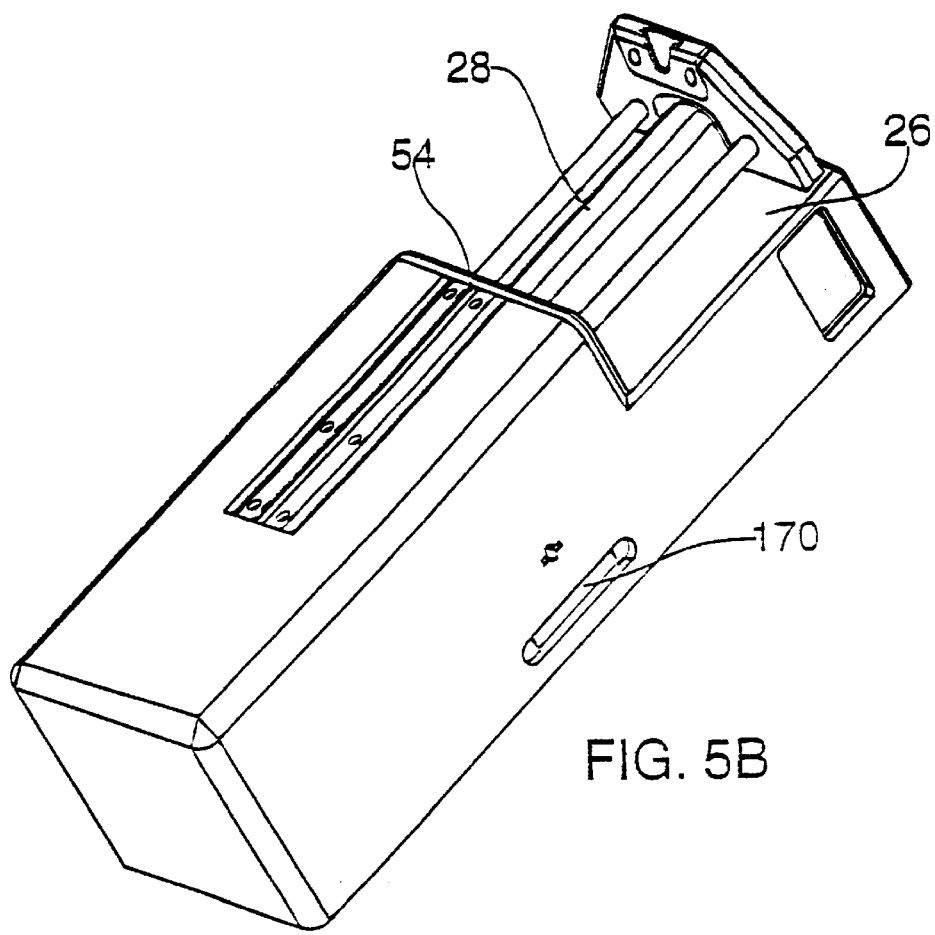
FIG. 5B shows an orthogonal view of the housing without the bracket.

On top surface 24, as seen more clearly in FIGS. 5A and 5B, there are provided two parallel elongated slots 32 and 34 and in between these slots there is formed a groove 36. The ends of each of the slots have lateral extensions 38 facing toward each other. Groove 36 ends adjacent to a transversal slot 54.

Figure 6:
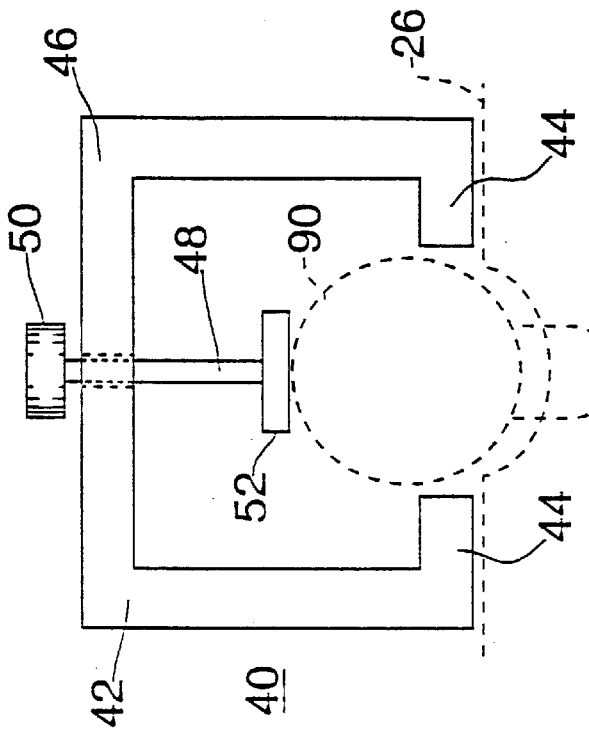
FIG. 6 shows an elevational view of a clamp for securing a syringe to the housing.
Figure 8:
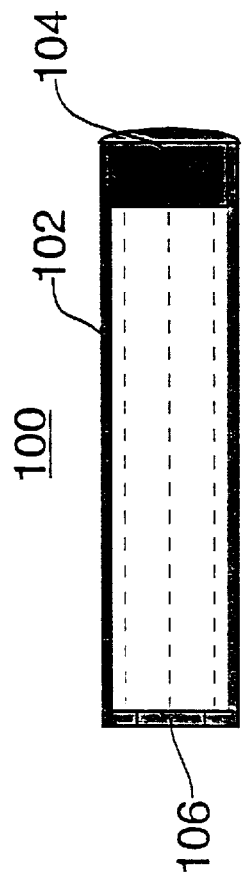
FIG. 8 shows a side sectional view of a prior art cartridge for a fluid.

Riding in slots 32, 34 is a clamp 40. As seen in FIG. 6, clamp 40 has a generally C-shaped body 42 terminating in legs 44 extending toward each other, and a web 46. A screw 48 with a head 50 extends through a threaded hole (not shown) in web 46 and terminates in a pad 52.

Clamp 40 is constructed and arranged so that its legs 44 fit into extensions 38 and allow the clamp to ride horizontally in slots 32. 34.

Platform 30 (seen in more detail in FIGS. 7A and 7B) is formed on its top surface 58 with a slot 56, which is provided on one side with a graduated keyway 60.

Inside the housing 22, there is provided a motor 66 (FIGS. 3 and 4) held securely within the housing. Threaded through the motor 66 there is a worm screw 72. The worm screw 72 is arranged so that as the motor 66 is activated, the worm screw 72 moves in one direction or another, dependent on its direction of rotation, in parallel with the longitudinal axis of the housing 22. One end of the worm screw 72 is non-rotatably attached to a pad 74, coupled to a platform 76. Disposed between platform 76 and pad 74 there is a load cell 78 arranged to transmit and measure the force between the pad 74 and platform 76. The load cell 78 is bidirectional so that it can measure both stress and strain dependent on whether the worm screw 72 is moving to the left or to the right as determined in FIG. 3. Two short rods 80 are used to couple the pads 74 to platform 76, to prevent the transmission of rotational forces generated by the motor 66 to the platform 76.

Two columns or rods 82, 84 extend between platforms 30 and 76 and secure these two members together. These rods 82, 84 are slidably supported by two pairs of bushings 68, 70 on the housing 22. Except for these bushings, the platforms 76 and 30 are floating respectively inside and outside the housing 22. Rods 82, 84 extend through wall 86 extending between surfaces 24 and 26 via holes (not shown). The rail 28 is hollow and aligned with the worm screw 72 to allow the worm screw 72 to move longitudinally along its axis through the housing 22.

Typically, the syringe 90 has a barrel 92 positioned in groove 36 so that its tab 95A (seen in FIG. 6) rests in slot 54. The syringe 90 also includes a plunger 94 reciprocated within the barrel 92 by a shaft 93. The shaft terminates in a finger pad 96. When the syringe 90 is seated in groove 36, the finger pad 96 rests in slot 56 of platform 30. In this position, the syringe 90 is secured to the housing 22 by inserting the legs 44 of clamp 40 into slot extensions 38 and advancing or sliding the clamp 40 to the left over the syringe 90 until it is positioned at the end of the syringe body 92 adjacent to the slot 54. In this position, the screw 50 is tightened, forcing the pad 52 to advance and engage the barrel of syringe 90. The groove 36 assists in the positioning of the syringe 90. The syringe terminates with a Luer lock 95 used to connect the syringe to tube 14.

It should be appreciated that the motor 66, pad 74, load cell 80, worm screw 72 and platform 76 are all located within housing 22. Platform 30 is disposed outside the housing 22. When the motor 66 is activated, as discussed below, it forces the worm screw 72 to move in one direction or another. The worm screw in turn forces the platforms 30, 76 and rods 82 and 84 to move in concert as well, thereby forcing the plunger 94 to move. The only elements which move in and out of the housing are the rods 82, 84. Hence most of the critical elements of the system are protected within the housing from tampering, or spilled fluids. Moreover, the drive mechanism 12 is adapted to receive and operate with syringes of various diameters and lengths. Similarly, the delivery tube 14, handle 16 and needle 17 may have any size desired.

In the embodiment discussed so far, it is assumed that a fluid is dispensed from the syringe 90 and, therefore, this syringe 90 must be preloaded with said fluid either by the manufacturer, or must be filled at the site by the clinician or an assistant prior to the start of any operation. In many procedures, however it is more desirable to provide the fluid to be dispensed in a cartridge such as cartridge 100 shown in FIG. 8. As can be seen in this Figure, cartridge 100 consists of a cylindrical barrel 102. At one end, the barrel 102 is provided with a piston 104 made of rubber or a similar resilient material which can be reciprocated through the barrel 102 to selectively eject the liquid contained therein. At the opposite end, the cartridge is provided with a seal formed of a membrane 106 which must be pierced before the contents of the cartridge can be dispensed.

Figure 9:
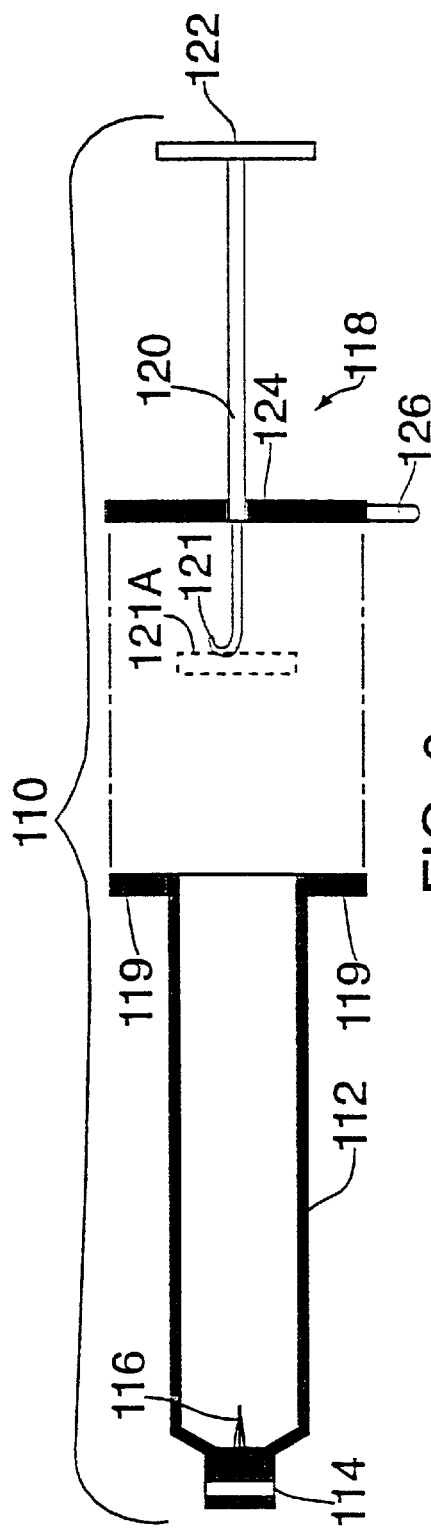
FIG. 9 shows a somewhat diagrammatic side view of an adapter for using the cartridge of FIG. 8 with the system of FIGS. 1–7.

FIG. 9 shows an adapter 110 provided to allow the driver of FIGS. 1–7 to dispense a fluid from cartridge 100. The adapter 110 includes a holder 112 adapted to hold cartridge 100. Holder 112 includes a first end having a connector 114 (for example a Luer connector) to connect the adapter 110 to delivery tube 14. Inside the holder 112, adjacent to connector 114, there is a spike 116 constructed and arranged to pierce the membrane 106 when the cartridge 100 is inserted into the holder 112. At the opposite end, the holder 112 is provided with radially extending projections 119 to secure the holder 112 to a drive mechanism 12. The cartridge holder 112 described so far is disclosed in commonly assigned copending application Ser. No. 09/028,009 filed Feb. 23, 1998 entitled "Dental Anesthetic and Delivery Injection Unit" incorporated herein by reference.

Adapter 110 further includes a coupling element 118 formed of a shaft 120 terminating at one end with a barb or hook 121 and at the opposite end with a thumb pad 122. The shaft 120 passes through a cap 124 adapted to mount on holder 112 by projections 119 engaging corresponding depressions (not shown) in the cap 124. Cap 124 is provided with a tab 126 extending radially and having the approximate shape of finger tab 95A on a standard syringe 90.

In order to mount cartridge 100 on the drive mechanism 12, the cartridge 100 is first inserted into the holder 112 from its rear end. Once the cartridge 100 is seated inside the holder 112, the shaft 120 is positioned in longitudinal alignment with the axis of holder 112 and then its hook 121 is pushed into the piston 104 until it is firmly engaged therewith. Next, the cartridge 100 is advanced toward the connector 114, so that the spike 116 penetrates the membrane 106 thereby providing an egress for the fluid contained therein. In order to ensure that the fluid does not spill, the tube 14 may be mounted on connector 114 first, however, this tube has been omitted in FIG. 9 for the sake of clarity.

Instead of a hook, a plunger 121A may be secured to the shaft 120 in such a manner that when this plunger is inserted into the holder 112, a vacuum/pressure coupling is generated between it and the piston 104. As a result, the longitudinal movement in either direction of the plunger causes the piston 104 to follow and thereby either push fluid into or out of the system.

Next, the cap 124 is coupled to the holder 112 by pushing the projections 116 into the appropriate depressions in the cap 124, thereby securing the cap to the holder 112. In this configuration, the cartridge 100, and adapter 110 have a configuration similar to a syringe 90 and can be mounted on the drive of FIGS. 1–7 just like a syringe, with the clamp 40 engaging cap 124, tab 126 extending into the slot 54, and thumb pad 122 engaging slot 56 on platform 30. With the adapter 110 in this position, motor 66 can be used to advance or retract shaft 120 and piston 104 into or out of the cartridge 100 either via the hook 121 or a plunger thereby causing the fluid to be ejected or aspirated as desired. The hook 121 (or the plunger) formed on the end of the shaft 120 is provided to ensure proper engagement and a solid mechanical coupling of the shaft 120 to piston 104 thereby ensuring that the piston 104 follows the movement of the shaft 120 and platform 30 in either direction.

Figure 10:
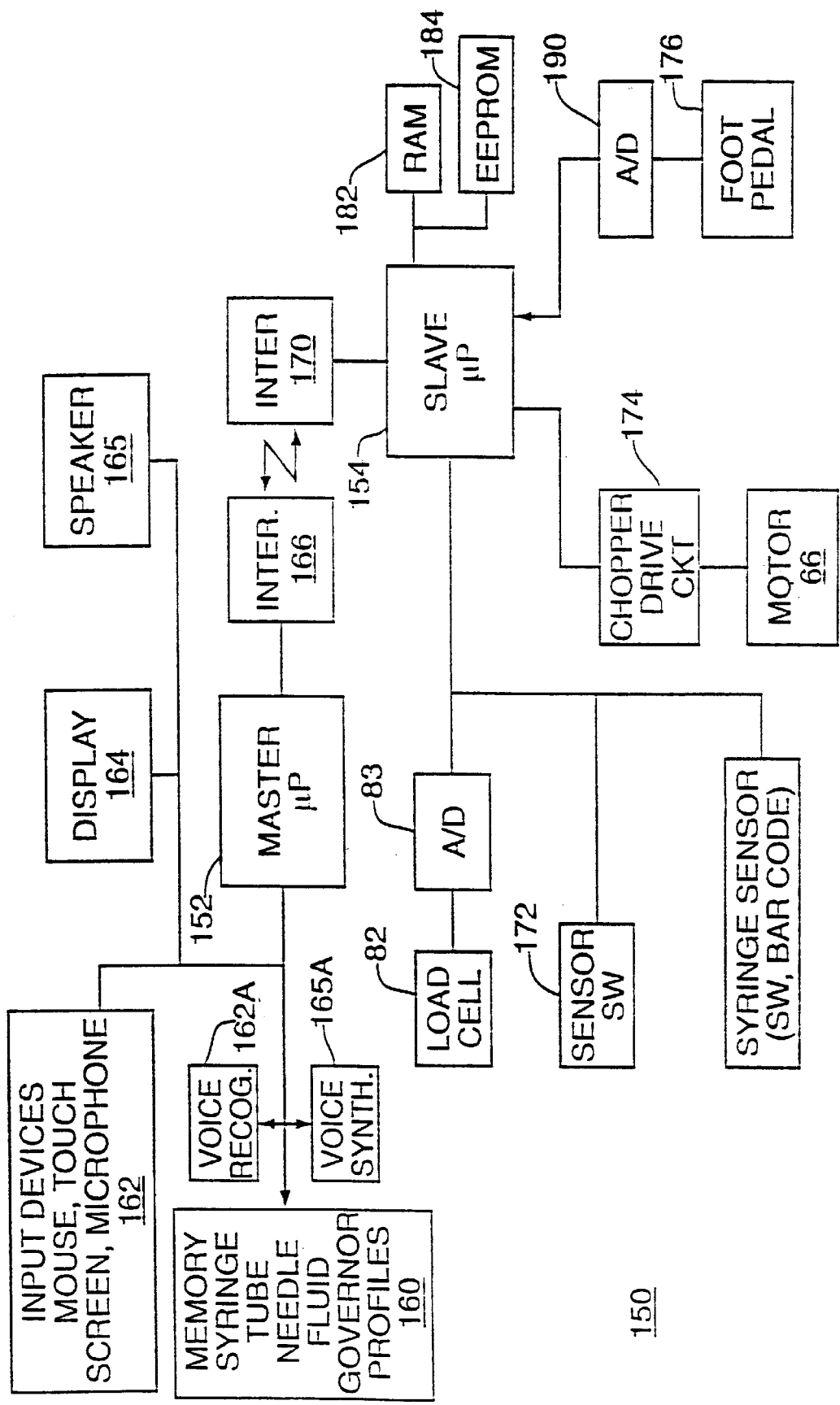
FIG. 10 shows a block diagram of the electronic controller.

FIG. 10 shows a block diagram of the electronic controller 150. The controller 150 includes two microprocessors: a master microprocessor 152 and a slave microprocessor 154. Slave microprocessor 154 is used to derive the signals that actually drive the motor 66 and to collect information regarding the position of the platforms 30, 76.

The master microprocessor 152 is used to collect information regarding the rest of the system, including the syringe 90, and its contents, the tube 14, the handle 16 and so on, and to generate control signals for the slave microprocessor 154 necessary for operating the motor 66 to deliver the contents of the syringe 90.

Physically, the slave microprocessor 154 and its associated circuitry are disposed within the housing 22. The master microprocessor 152 is incorporated into control unit 18 which is coupled to the housing 22 through cable 20 as shown in FIG. 1.

As seen in FIG. 10, microprocessor 152 is associated with a memory 160, input devices 162, display devices 164 and an interface 164.

Memory 160 is used to store programming and data for the master microprocessor 152. More specifically, the memory 160 is used to store six or more data banks, each of said data banks being dedicated to the following information: (a) syringes; (b) tubing; (c) needles; (d) fluids; (e) governor parameters; and (f) profiles consisting of a plurality of parameters for a particular procedure to be performed. Each of these parameters is used to determine the control signals generated for the slave microprocessor 154. Each of these data banks contains the appropriate parameters for various commercially available products, or alternatively, parameter data derived using a specific algorithm. Information regarding the various elements for a particular configuration is entered through input devices 102 and is confirmed on the display device 164. These input devices may include a keyboard, a touch screen, a mouse, as well as a microphone. If a microphone is included, voice commands are interpreted by a voice recognition circuit 162A.

The display device 164 is further used to provide an indication as well as instructions on the operation of the system 10. The commands for the operation of motor 66 are generated by master microprocessor 152 and transmitted to an interface 162. Microprocessor 152 is further provided with a speaker 165 used to provide various oral messages, including spoken pre-recorded or synthesized words, (generated by a voice synthesized circuit 165A) chimes, and so on, to provide instructions to the clinician and to provide other information about the current status of the whole system and its elements without the need for the clinician to look at the displays all the time.

The slave microprocessor 154 receives these commands through cable 20 or other connection means and interface 170.

Also associated with the slave microprocessor 154 are one or more position sensors 172 and a chopper drive circuit 174. As previously mentioned, the force between platform 76 and pad 74 is measured by a load cell 78. This load cell may be for instance a Model S400 load cell made by the SMD, Inc. of Meridien, Conn.

Also associated with slave microprocessor 154 is a foot switch or pedal 176. Preferably foot pedal 176 consists of an air chamber with a flexible side wall, said side wall being arranged to change the volume of air and pressure within said chamber in response to activation by a human operator. A pressure sensor (not shown) is part of the foot pedal and is arranged to provide information about said pressure to slave microprocessor 154 via a corresponding A/D converter 190. Foot pedals of this kind are well known in the art and therefore its details have been omitted.

Figure 11:
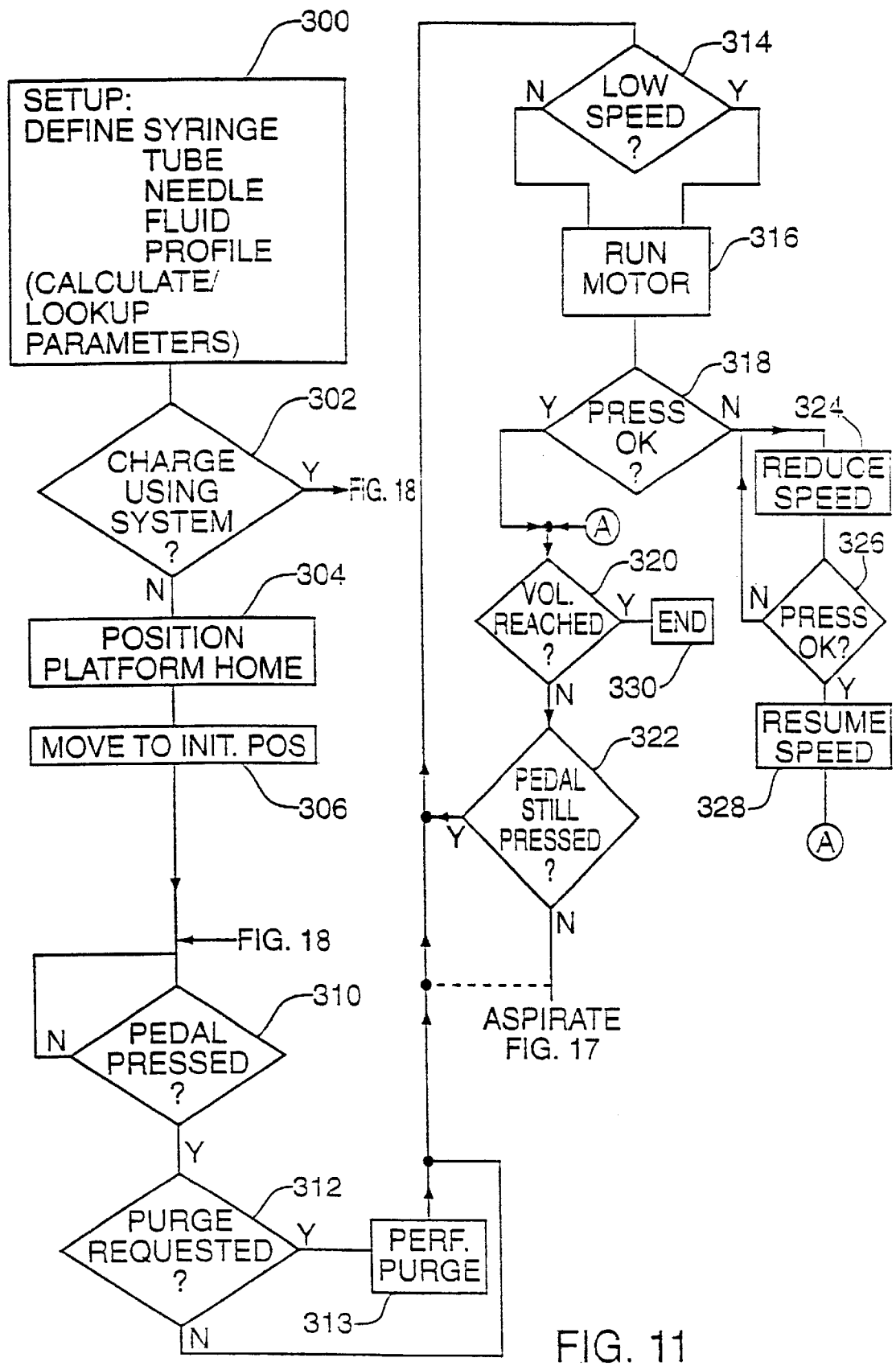
FIG. 11 shows a general flow chart for the operation of the controller of FIG. 10.

The sequence of operation for the system 10 is now described in conjunction with FIG. 11. Starting in step 300, the system is first set up. Since this step involves exchange of information with the clinician and the outside world, it is performed by the master microprocessor 152.

Figure 12A:
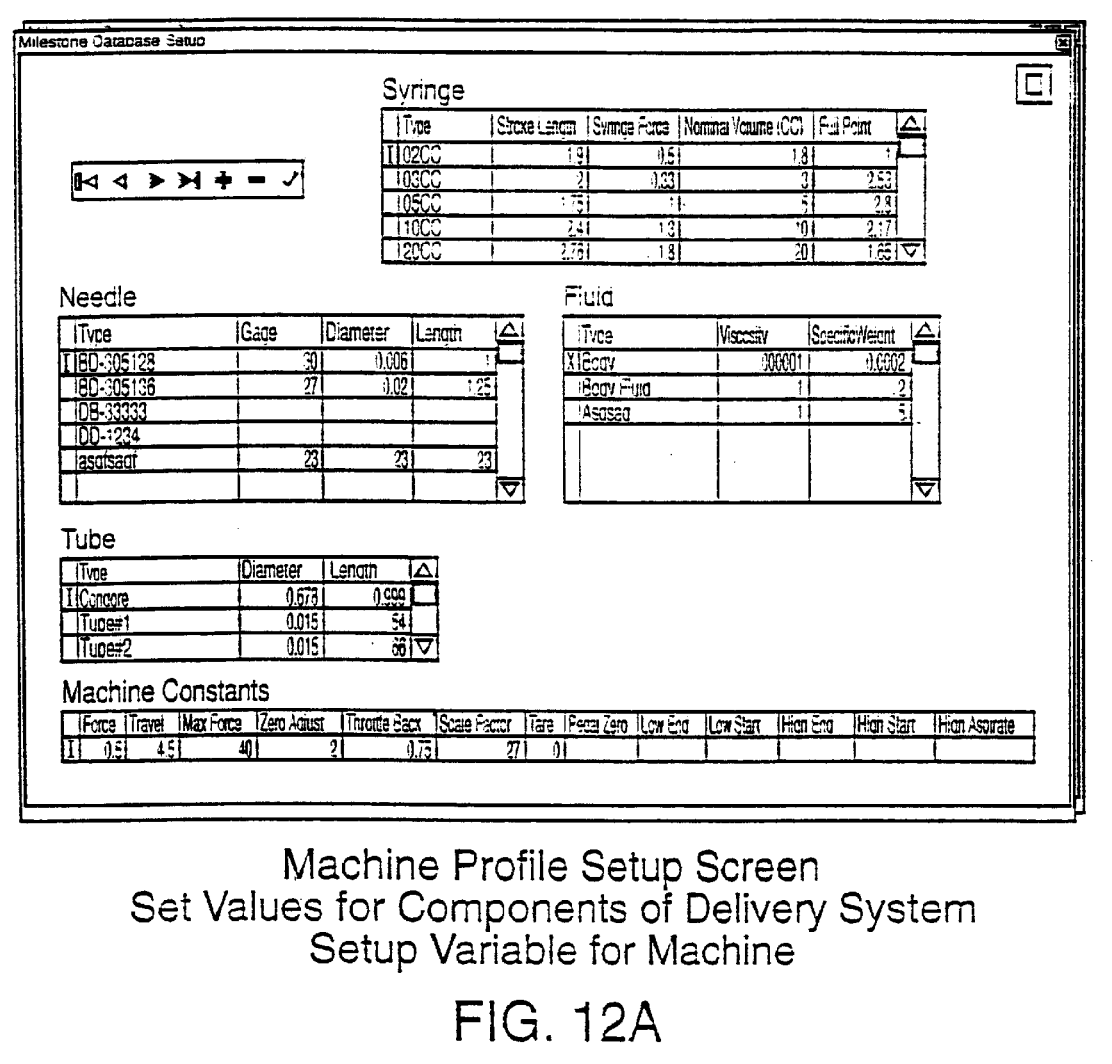

Step 300 involves, first, having the clinician enter the following information: type of syringe being used, type (i.e. size and length) of tube 14, type of needle being used, and name or other identification of the fluid in the syringe. This information may be entered manually by the clinician using an input device such as a keyboard or a touch screen disposed in the screen. Alternatively, a plurality of the corresponding items (for example, syringes) may be retrieved and displayed from the data bases and then presented to the clinician. The clinician then uses a standard pointing device such as a mouse or a touch screen to select the appropriate syringe. Alternatively a voice command may be used for this selection. FIG. 12A shows a typical screen for designating or selecting a syringe. As seen on this screen, once a syringe is selected or designated, its physical characteristics such as length, nominal volume, stroke length, syringe force are retrieved from the data bank and displayed. After the needle and fluid have been designated, their characteristics are retrieved and displayed as well.

Some of the information, such as, for instance, the length of the tube 14 must be entered manually since it would be difficult for the system to determine. However other information, as well as various operational parameters are determined automatically. For example, the identify of a syringe may be encoded into a portion of the syringe and read by the system. As described below, one required parameter is the cross sectional area A of the syringe. This is determined by dividing the volume by the stroke or length of the syringe.

Once the information regarding the components of the system are entered or otherwise selected, another screen (FIG. 12B) is presented to the clinician. This screen is used to either provide information to the clinician or to allow the clinician to enter certain additional operational parameters required to complete the setup.

Figure 12B:
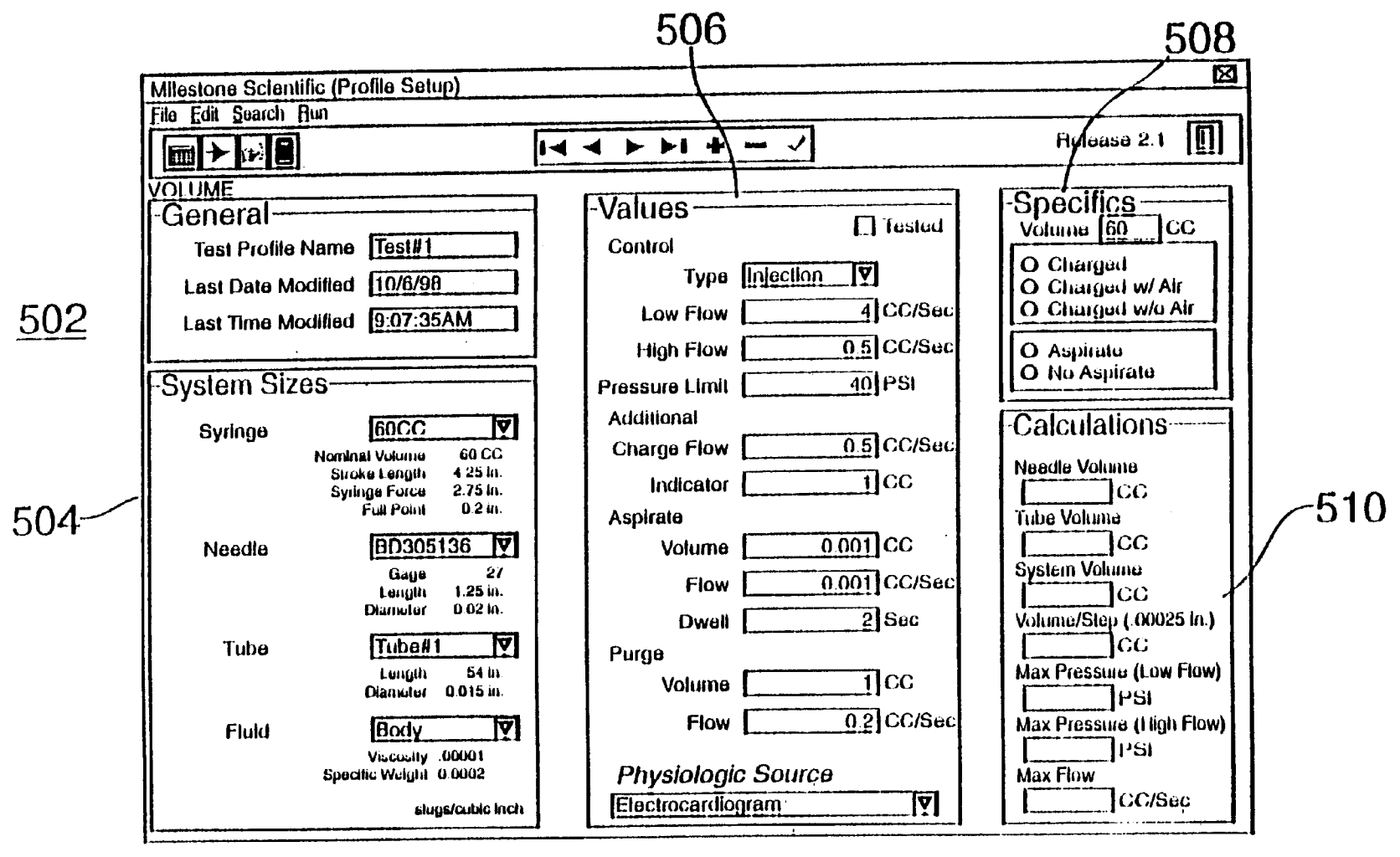

The screen of FIG. 12B has five general areas designated 502, 504, 506, 508 and 510. In area 502, some general information is provided or selected by the clinician including a designation for the profile to be used for the current procedure, i.e. 'PERIODONTAL LIGAMENT INJECTION'. In area 504, the parameters from screen of FIG. 12A are repeated in an abbreviated format, thereby indicating the syringe, needle, tube and fluid information.

In area 506 the clinician selects the type of operation he requires (i.e., injection) the high and low flow rates, and the optimal pressure limit. As previously mentioned, this last parameter is very important because it controls the amount of pain and tissue damage that the patient may suffer during the procedure. Additional parameters may also be selected in this area, such as charge flow rates, aspiration volume and flow rate, purge volume and flow rate and so on.

In area 508 the clinician designates the total amount of fluid to be dispensed, and whether (a) the syringe is charged, (b) is to be charged with air; or (c) to be charged without air. The clinician also selects in this area whether he will use aspiration or not. Finally area 510 is used to indicate various parameters calculated from the information previously received or selected, including the system volume, maximum flow rates, maximum pressure and so on.

In one embodiment of the invention, the system, and more particularly the master microprocessor 152 then uses these parameters to retrieve from the profile data base a profile which determined the sequence and programming characteristics required to deliver the fluid to through the needle at the requested, or optimized rate. The profile for each particular syringe-tube-needle combination is calculated and stored into the memory earlier. These profiles have unique characteristic for each type of surgical procedure. For example, a profile for a PDL (periodontal ligament) is different from a profile for a cranial subcutaneous anesthesia delivery. Only a single group or family of profiles associated with a specific procedure may be stored in the memory of the master microprocessor since other such profiles are superfluous.

Alternatively, the master microprocessor 152 may be programmed to perform the calculations necessary to generate the profiles. However it is expected that for most applications, the profiles will be calculated a priori and programmed or stored into the data base, as discussed above.

After the setup procedure is completed, in step 302, a test is performed to determine if the clinician desires to fill the syringe 90 using the subject device or not. In many instances, it is expected that the clinician either preloads the syringe manually, or uses a prefilled syringe or cartridge. If the syringe is loaded or charged off the device, then in step 304, the master microprocessor 152 sends a command to the slave microprocessor 154 to move the platform 30 to an initial position.

Referring to FIG. 10, the microprocessor 154 is associated with the load cell 80 through an AD converter 83, a Ram 182, an EEPROM 184, and a limit switch 172. Using information derived from these elements, whose functions are described in more detail below, and in response to commands from the master microprocessor 152 via interface 170, the slave microprocessor 154 controls the operation of motor 66. More specifically the slave microprocessor 154 operates a chopper drive circuit 188 which then generates stepping pulses to motor 66 to cause said motor 66 to turn in one of two directions by a discrete angular increment. The frequency of these pulses determines the speed of the motor. Separate speeds may be used for high flow rate, low flow rate purge, aspiration or charging. The clinician selects the values for all these speed parameters and the microprocessor then calculates the corresponding motor speed (i.e. step frequency) using the dimensions of the syringe and the fluid delivery system.

The microprocessor 154 keeps track of the position of the platforms 30, 76 by counting the steps taken by motor 66. Alternatively, or in addition, other sensor switches may also be provided to detect and conform the location of the platforms, such as platform 76 at several locations along its path of travel. In the preferred embodiment, at least one sensor switch 172 is provided which defines the home position for the platform 76. All other positions of the platform 76 are computed from this home position. For example the home position could the extreme left position shown in FIG. 4.

Motor 66 is preferably made with rare earth permanent magnets so that it can be relatively compact and yet generate a large torque.

Getting back to FIG. 11, in step 304, the microprocessor 152 sends a command to order the microprocessor 154 to move the platform 76 to the home position. A list of all commands of this type is stored in the memory 160 as part of the governor data base. The microprocessor 154 activates the motor until the platform 76 reaches the home position, and this position is verified by an output from sensor 172 and is reported to microprocessor 152. Next, in step 306, microprocessor 152 orders the platform 76 to be moved to an initial position. This initial position is a function of the selected syringe and the amount of fluid contained in the syringe, and is defined by the profile stored in the profile data base.

Figure 13:
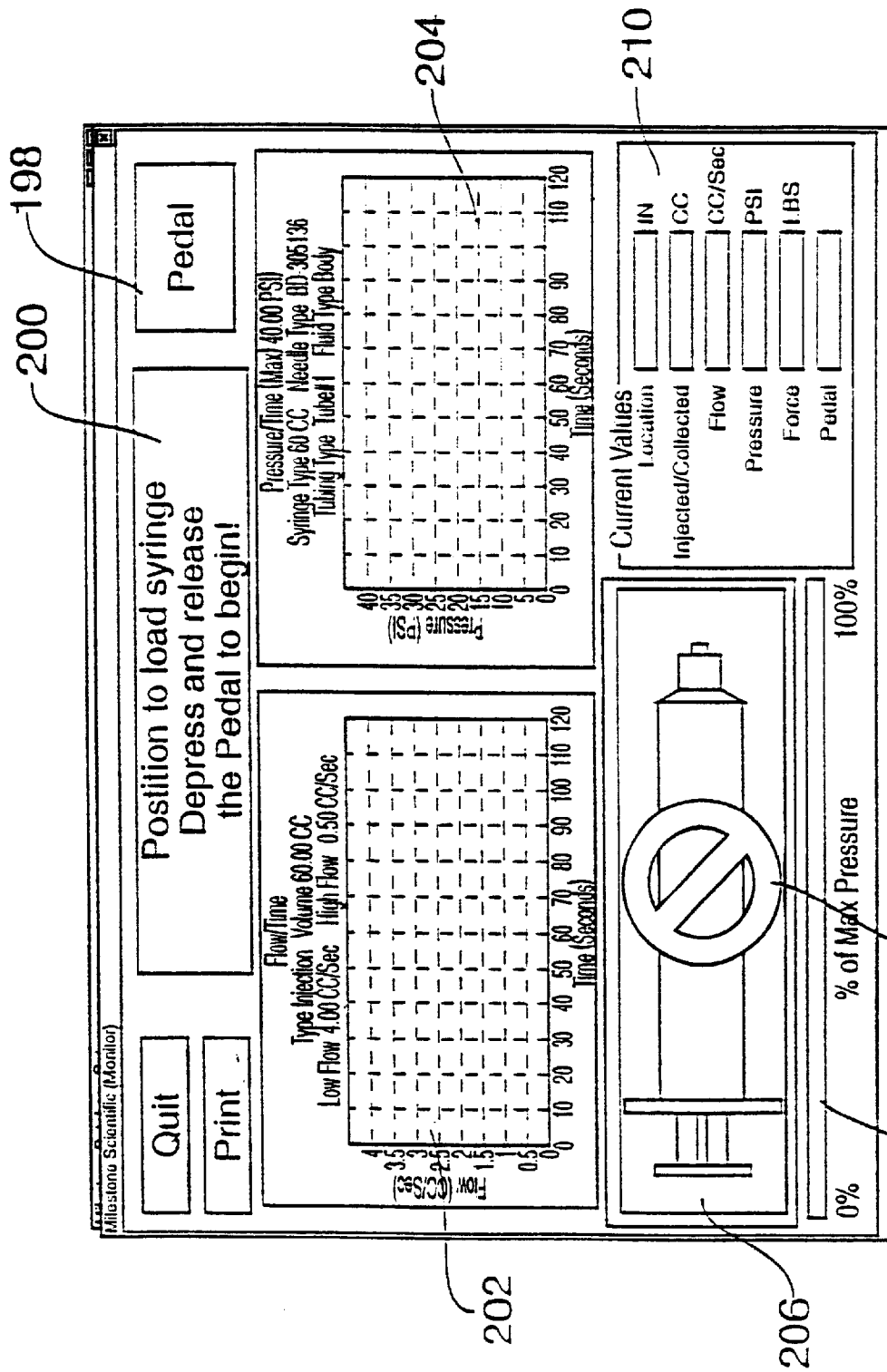
FIG. 13 shows a typical display shown to the clinician during the setup process.

The system 10 is now ready to accept a filled syringe. FIG. 13 shows a typical screen on display 164 which may be shown to the clinician at this time. This display includes a several soft or programmed 'buttons' which may be activated by the clinician to initiate certain commands as well as several display regions in which information is provided to the clinician. In this particular instance, the display shows the following buttons 198 labeled: Quit, Print, Pedal. In other instances other buttons may be shown.

In addition, the display of FIG. 13 includes the following information areas: a message area 200 in which instructions are provided for the next phase; or a message is displayed informing the clinician of the step or processes being currently performed; two graphs 202, 204 in which the fluid flow and the exit pressure are shown as a function of time, a syringe icon 206, a pressure gauge 208 which shows the current exit pressure as a percentage of the maximum allowable pressure (another parameter developed as part of the profile), and another set of gauges collectively marked 210 and indicating the following parameters: location of the platform 76 (and therefore the plunger within the cylinder) in inches with respect to the initial location, the volume of fluid that has been injected (or collected in case of biopsy), the current flow rate in cc/sec, the current pressure (psi), the force being applied and the force being applied by the pedal switch 176. At the beginning of step 306, the display areas 202, 204, 208 and 210 show no values for the corresponding values and the icon 206 has an indication 212 to show that no syringe has been detected. Display 200 shows a message instructing the clinician to load the syringe 90 and depress the pedal 176.

The clinician can now take a filled syringe and place in groove 36 with the finger tab 95A extending into slot 54 and the thumb tab 96 inserted into the slot 56 of platform 30. As mentioned before, the motor 66 has moved the platforms 76, 30 to the initial position. This initial position is defined as the position at which the filled syringe 90 can be mounted with its thumb pad 96 fitting into the slot 56. It should be noted that the system will not accept syringes in any other position. In effect, the software is used to ensure that the correct syringe with the correct amount of fluid is loaded, and that another syringe cannot be loaded by mistake.

The system waits for the syringe to be mounted in step 310. The clinician can indicate that the syringe is mounted either by activating physically foot switch 176 momentarily or activate the pedal button 198 on the screen. When the pedal signal is sensed the drug delivery can proceed. First the red stop symbol 212 is turned off. In step 312 the system checks if the clinician has requested a purge. If so, a purge is performed in step 313 during which the drug delivery system is freed of potential air bubbles. The volume of the needle, the handle and tube are known and therefore the volume of fluid to be purged is easily calculated.

Figure 14:
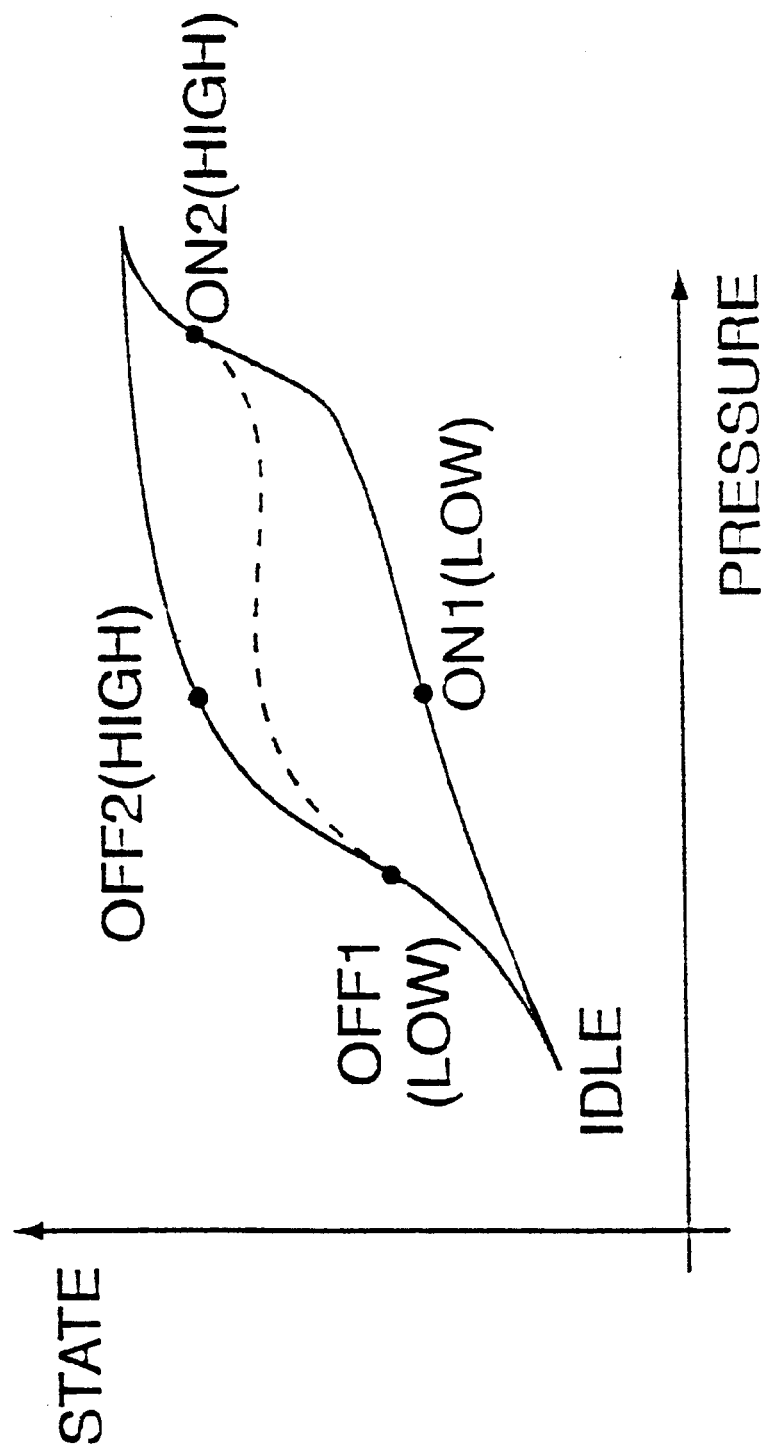
FIG. 14 shows graphically the control signals derived from a foot pedal.

As mentioned above, preferably, the foot switch 176 includes an air bellows and an air pressure sensor (not shown). The output of the air pressure sensor is fed to the A/D converter 190 and the digital equivalent of the foot switch output is fed to the microprocessor 154. The microprocessor 154 uses this sensor in conjunction with a look-up table stored in the EEPROM 184 to determine or generate a switch indication signal indicative of the position of the switch. It has been found that, for best response and sensitivity, the position of switch is translated into four different positions or states using hysterisis. In other words, as indicated in FIG. 14, initially the switch is in an idle state. As the switch is depressed, its internal pressure increases. When it reaches a first value ON1, the microprocessor 154 generates a LOW FLOW command. If the pressure increases but does not exceed a level ON2 then, the LOW FLOW command is maintained. If the pressure is reduced to below a level OFF1, then the idle state is indicated. Typically the pressure OFF1 is lower than ON1. If the pressure exceeds ON2 then a HIGH FLOW command is generated. This HIGH FLOW command is not turned off until the pressure drops below a pressure level OFF2 which is lower than ON2.

Referring back to FIG. 11, after purging, if any, in step 314 position or state of the pedal 176 is determined. If a LOW FLOW command is received, then the drug is dispensed at a low rate. If a HIGH FLOW command is received, the drug is dispensed at a high flow rate. The actual values for HIGH and LOW FLOWS have been previously set as discussed above.

Figure 15A:
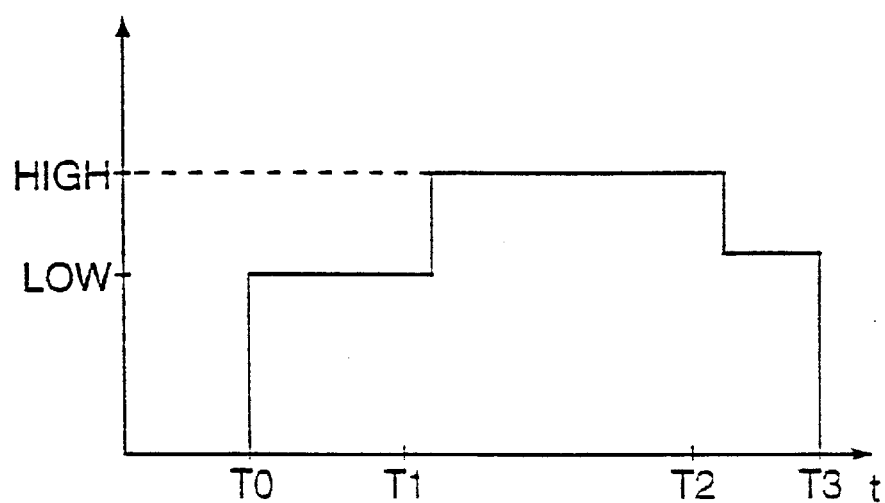
FIGS. 15A and 15B show typical time dependent curves for the fluid flow and the exit pressure, respectively.
Figure 15B:
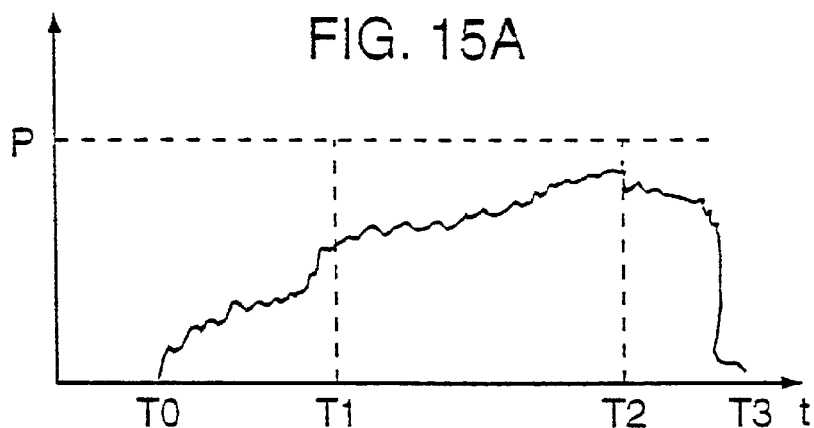

Once the pedal is depressed, the motor is initiated and is run at a predetermined rate corresponding to the rate of flow requested (step 316). A typical drug delivery is shown in FIGS. 15A and 15B as they would appear in areas 202 and 204 respectively. As seen in these FIGS. The flow rate builds up relatively quickly to a first value LOW at T0 and levels off to a constant level. The exit pressure starts climbing in a somewhat irregular manner determined by the tissue resistance to the fluid flow and other factors. At T1 the pedal is activated to a higher level HIGH and the fluid flow rate climbs to this new rate. The exit pressure continues to rise as well. At T2 the pedal may be released back to the lower level LOW. As this process continues, the microprocessor 152 continuously monitors various pressure parameters (step 318), and it accumulates the total volume dispensed and compares this current volume to the total requested volume (step 320). If it has not been reached, then in step 322 a check is performed to determine if the pedal 176 is still pressed. If it is, then step 314 is repeated. If it is not, then it is assumed that an aspiration is requested, and accordingly an aspiration routine is performed as described below in conjunction with FIG. 17.

In step 318 the current pressure indicated by the load cell is checked against a threshold which is the peak pressure that is safe for the system. This pressure level depends on the components selected for the system. In addition, in step 318 the exit pressure level is also monitored. As discussed above, it has been found that the fluid pressure during an injection plays a very important role in the amount of pain and tissue damage that a patient feels during an injection. At low levels of pressure, the pain is minimal so that the patient is almost comfortable. However, if the pressure increases beyond a certain level, the injection becomes very painful. Therefore an important consideration in the present invention is the control of the flow rate in a manner that ensures a low exit pressure level.

More particularly, in step 318 if either pressure (i.e., the pressure within the system or the exit pressure) is found to be excessive, then in step 324 the flow rate is reduced. In step 326 the pressures are checked again. If either pressure is still too high, the flow rate is reduced again in step 324. If acceptable, then the flow rate is resumed in step 328 and the process continues with step 320.

Figure 16A:
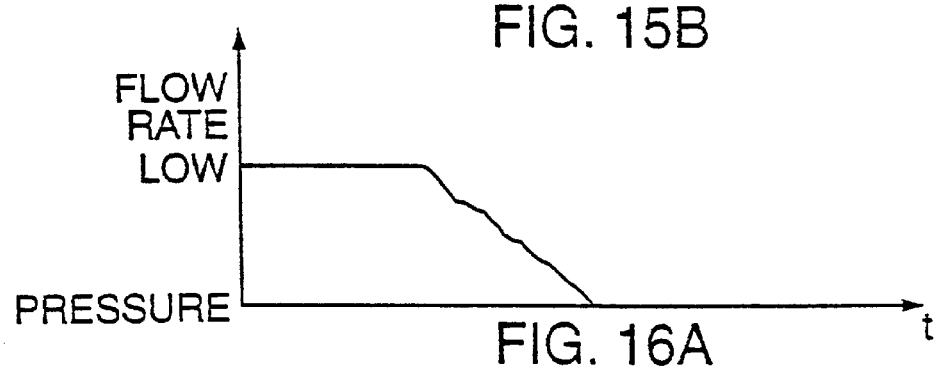
FIGS. 16A and 16B show time dependent curves for fluid flow and the exit pressure when said pressure exceeds a threshold level.
Figure 16B:
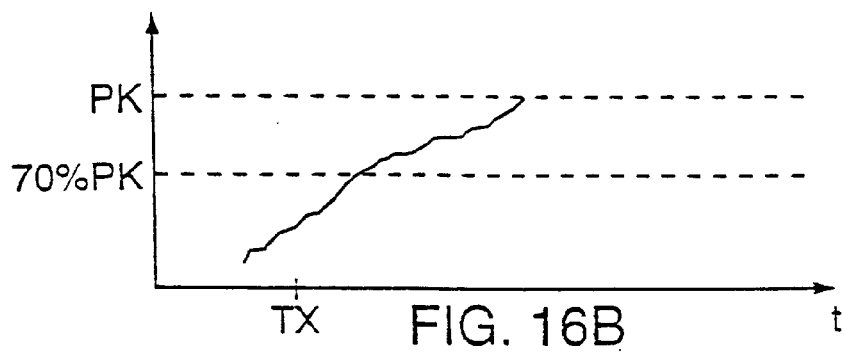

The flow rate and various other parameters are shown to the clinician on display shown on FIG. 13 so that he should be able to see very easily what is happening. In all likelihood, an increase in pressure such as shown in FIGS. 16A and 16B at TX is caused either by a blockage or the needle hitting a bone. Whenever an abnormal pressure is detected, a visual as well as an audible alarm is provided. Therefore the clinician is expected to take some evasive action to stop the high pressure. However, if the blockage continues and the pressure keep increasing the flow rate is gradually decreases as seen in FIG. 16A until it stops altogether.

Getting back to step 320, when the designated volume has been reached or if a stop command is issued by the clinician, in step 330 an end subroutine is performed. During this subroutine, the forward motion of the syringe plunger stops, and a message is displayed for the clinician to withdraw the needle. The clinician can withdraw the needle, decouple the tube 14 from the syringe 90 and throw the tube 14 the handle 16 and needle 17 away. Optionally, an aspiration subroutine, discussed below is also performed to ensure that fluid from the needle 17 does not spill.

In many instances, aspiration is desirable during a drug infusion process. For example, for the infusion of an anesthetic, after the insertion of the needle, aspiration is required to check if the needle tip is disposed in a blood vessel. In this instance, aspiration causes some blood to be withdrawn from the vessel. This blood becomes visible in the handle 16 or the hub of the needle 17.

Figure 17:
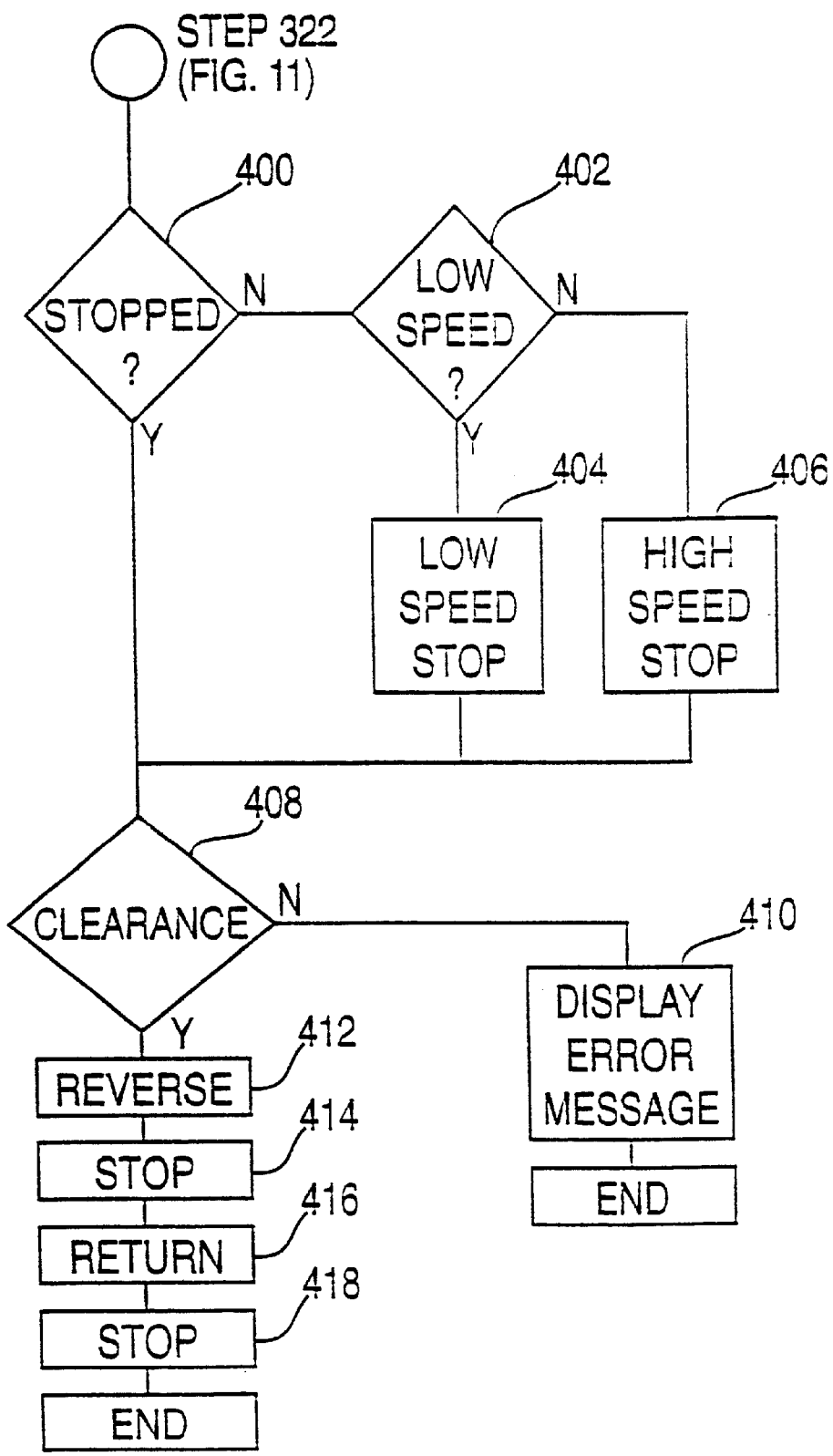
FIG. 17 shows a flow chart for aspiration.

As seen in FIG. 11, if in step 322 the pedal is found released, an ASPIRATE routine is initiated as shown in FIG. 17.

More particularly, in step 400 a check is performed to determine if the plunger 94 in the syringe 90 is stopped. If it is not then in step 402 a check is performed to determine if the plunger is moving at a low speed. If it is, then in step 404 low speed stop routine is performed to slow down and stop the motor. Otherwise in step 406 a high speed stop is routine is performed to slow down and stop the motor.

Figure 3:
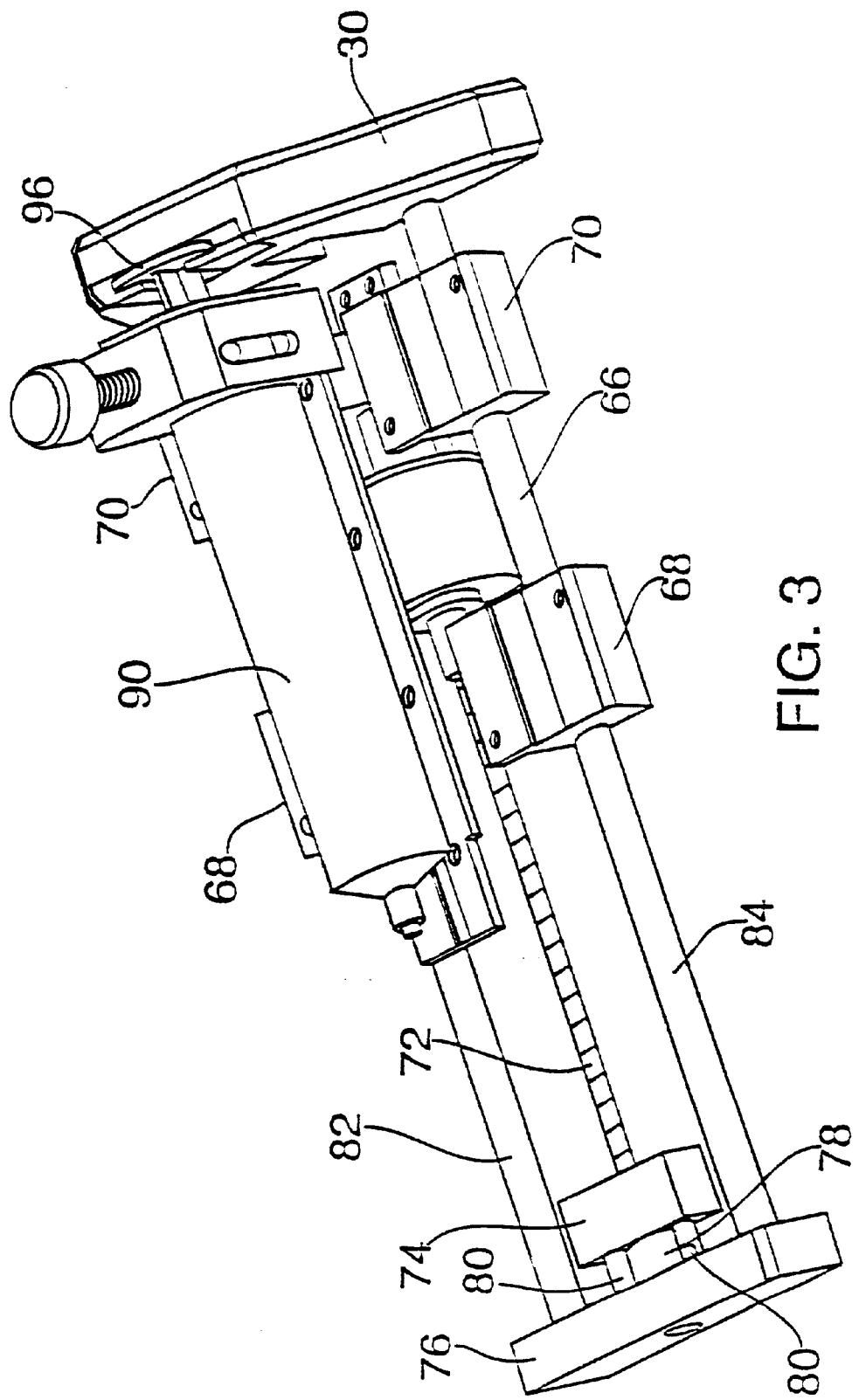
FIG. 3 shows the major elements of the drive mechanism.
Figure 4:
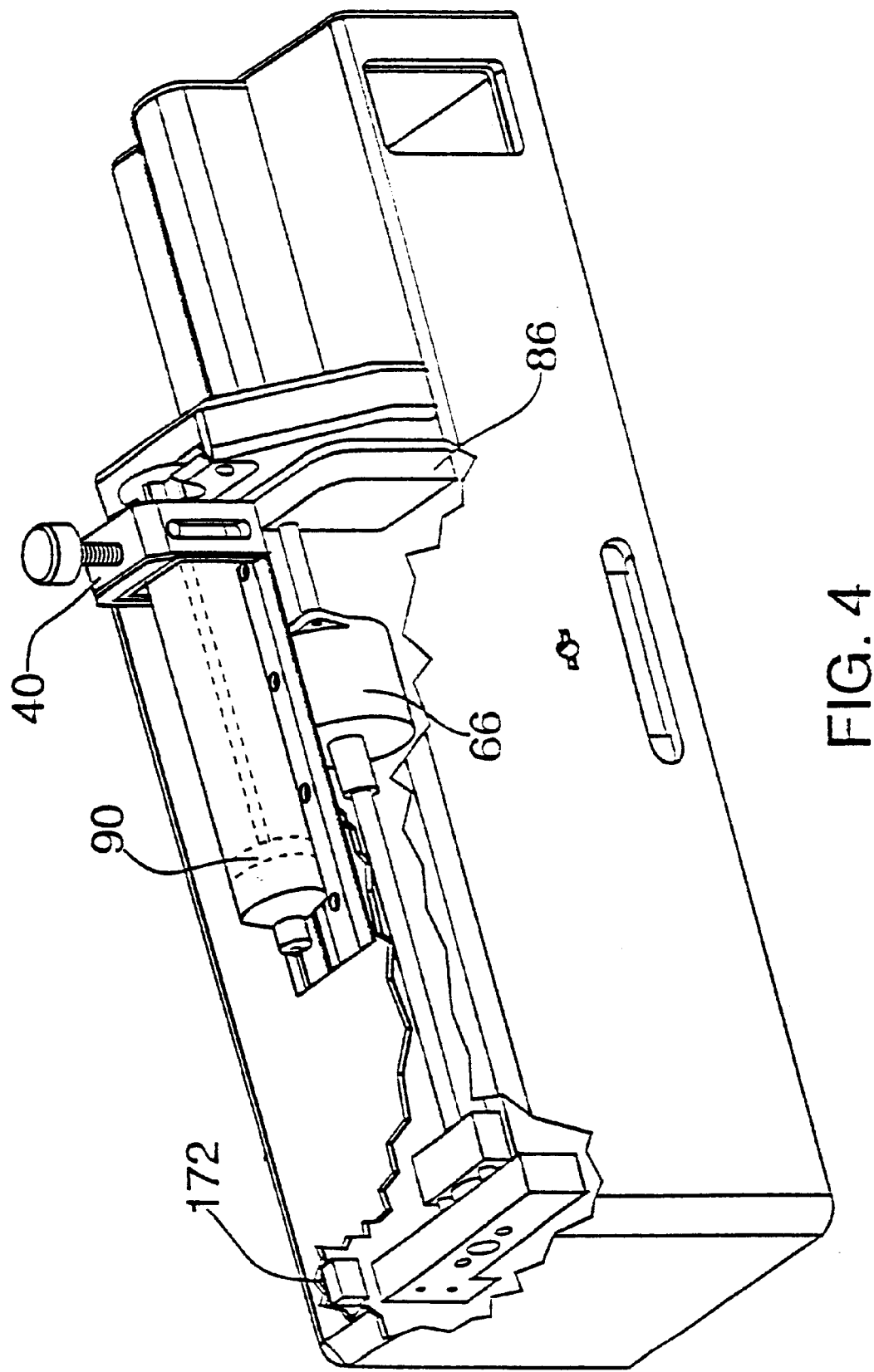
FIG. 4 shows how the elements of the drive mechanism of FIG. 3 are disposed in the housing.

In step 408 a check is performed to determine if there is sufficient clearance to perform an aspiration. Referring to FIG. 3, at the moment an aspiration command is received, the plunger 94 could be in its rightmost position so that retreating it further from the syringe may cause it to fall out. Obviously such an event is not desirable. Therefore, in step 408 a check is performed to determine from the location of the plunger and the length of the syringe whether it is safe to perform an aspiration without the plunger falling out. If it is not, then the process is stopped and in step 410 an error message is displayed to the clinician to indicate that it is unsafe to aspire at this time.

Otherwise in step 412 the motor is reversed and runs in the opposite direction for a predetermined time causing the plunger 94 to retract. After the plunger is moved the predetermined distance, it is stopped (step 414). The plunger is then moved forward again (step 416) until it is returned to its original position at step 408. The motor is then stopped (step 418).

Steps 416 and 418 may be omitted if the aspiration is performed at the end of the process when the needle is retracted from the tissue.

In this manner the subject system is used to deliver an anesthetic for a particular procedure. For example, if the procedure is a periodontal ligature then the following parameters are applicable:

| | |
|---|---|
| Syringe type: | Dental Cartridge |
| Syringe size: | 1.8 cc |
| Drug: | Local Anesthetic (Lidocaine HCl 2%, and epinephrene 1:100,000) |
| Specific weight of drug: | 0.0361 |
| Tube inner diameter: | 0.015 in |
| Tube length: | 60 in |
| Needle type: | BD 30 G ½ |
| Needle length: | 0.5 in |
| Needle inner diameter: | 0.006 in |
| Low Speed: | 0.0059 cc/sec |
| High Speed: | 0.370 cc/sec |
| Peak Pressure: | 250 psi. |

When a normal syringe and needle of the dimensions described above are used to inject the same fluid manually, it has been found that an exit pressure of up to 660 psi or more is generated.

For other procedures, different syringes, drugs, tubes and/or needles are selected.

As discussed above, a critical parameter being monitored by the subject system is the fluid exit pressure at the tip of the needle, i.e., the pressure within the tissue as the fluid exits from the needle. This is the pressure which is indicated by the graphs of FIGS. 15A and 16A. However, this pressure is very difficult to measure directly. Therefore in the present invention rather then taking a direct measurement, an indirect measurement is obtained. More specifically, the desired exit or needle pressure Pn is derived from the force indicated by the cell 78 and the physical characteristics of the system. More particularly, it has been found that the exit pressure during a steady state (i.e. with the plunger moving at a constant velocity) can be expressed as follows:

$$Pn = Ps - dVhn + dVhl - d(Fl + Ft + Fn) \text{ where}$$

Ps is the pressure generated at the plunger/fluid interface by the movement of the plunger;

Vhn is the velocity head in the needle;

Vhl is the velocity head in the syringe;

d is the specific weight of the fluid; and

Fl, Ft and Fn represent frictional losses due to flow in the syringe, tube and needle respectively.

There are some other minor pressure losses in the system which have found to be less than 1% and therefore can be ignored.

The frictional losses are determined empirically and stored as part of the profile for each element of the system. For example typical values for Fl, Ft and Fn have been found to be:

$$Fl = 0.1\%; Ft = 89\%; Fn = 11\% \text{ of the total head loss.}$$

The density of the fluid is known and is usually close to the density of water.

The velocity heads are calculated using the expression:

$$Vhl = \alpha * Q^2 d/[(\pi/4)^2 D^4 (2g)]$$

where α is the kinetic energy factor related to the Reynolds number and for laminar flow has a value of 2;

Q is the respective fluid flow, as indicated in FIGS. 15A and 16A;

g is the gravitational constant; and

D is the inner diameter of the respective member, i.e. the syringe for Vhl and the needle for Vhn.

An additional factor for acceleration must be added whenever the motor speeds up or slows down. This factor is given by the following expression:

$$Ms*a/As + Mt*a/At + Mn*a/An$$

where Ms, Mt and Mn are the fluid masses respectively in the syringe, tube and needle and As, At and An are the corresponding cross sectional areas.

Figure 20:
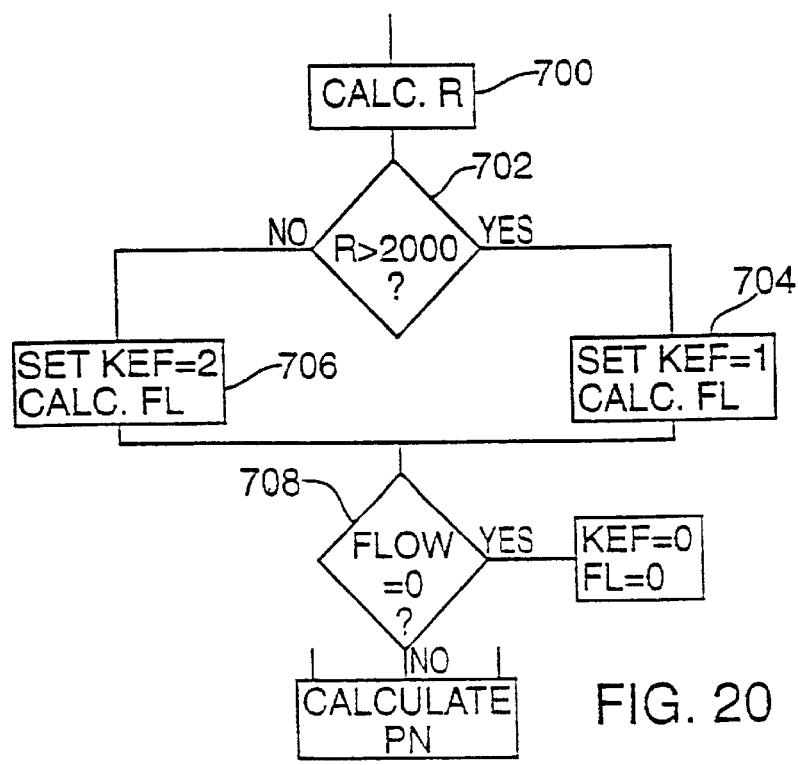
FIG. 20 shows a flow chart for determining a typical component contributing to the exit pressure determination.

A program for determining the exit pressure (designated in the program listing as 'Needle Pressure') is attached at the end of this specification. As can be seen from this listing, and in the flow chart of FIG. 20, in order to calculate the exit pressure, first the friction losses in each of the tree components (the syringe, tube and needle) are determined as follows. In step 700 a Reynolds number is determined from the flow rate, the component diameter and viscosity. If the Reynolds number is over 2000 (indicating a turbulent flow) then (step 702) a parameter Kinetic Energy Factor is set to 1 and the Friction Loss is calculated using the Reynolds number (step 704).

For R<2000 (step 706) the Kinetic Energy Factor is set to 2, and a different expression is used to determine (step 706) the Friction Loss. (based on the fluid viscosity the flow rate and component diameter). In the absence of a flow, the Friction Loss and the Kinetic Energy Factor are both set to 0. (708). Next, when the parameters from all the components are calculated, the flow loss for each component is calculated, the stopper force is calculated, and all these parameters are used to obtain the exit or needle pressure (step 712).

Every time the microprocessor 152 checks the pressure (Step 318 in FIG. 11), it actually calculates the exit or needle pressure Pn as discussed above. FIGS. 15B and 16B show a normal pressure and an abnormal pressure curve respectively using these expressions.

Figure 18:
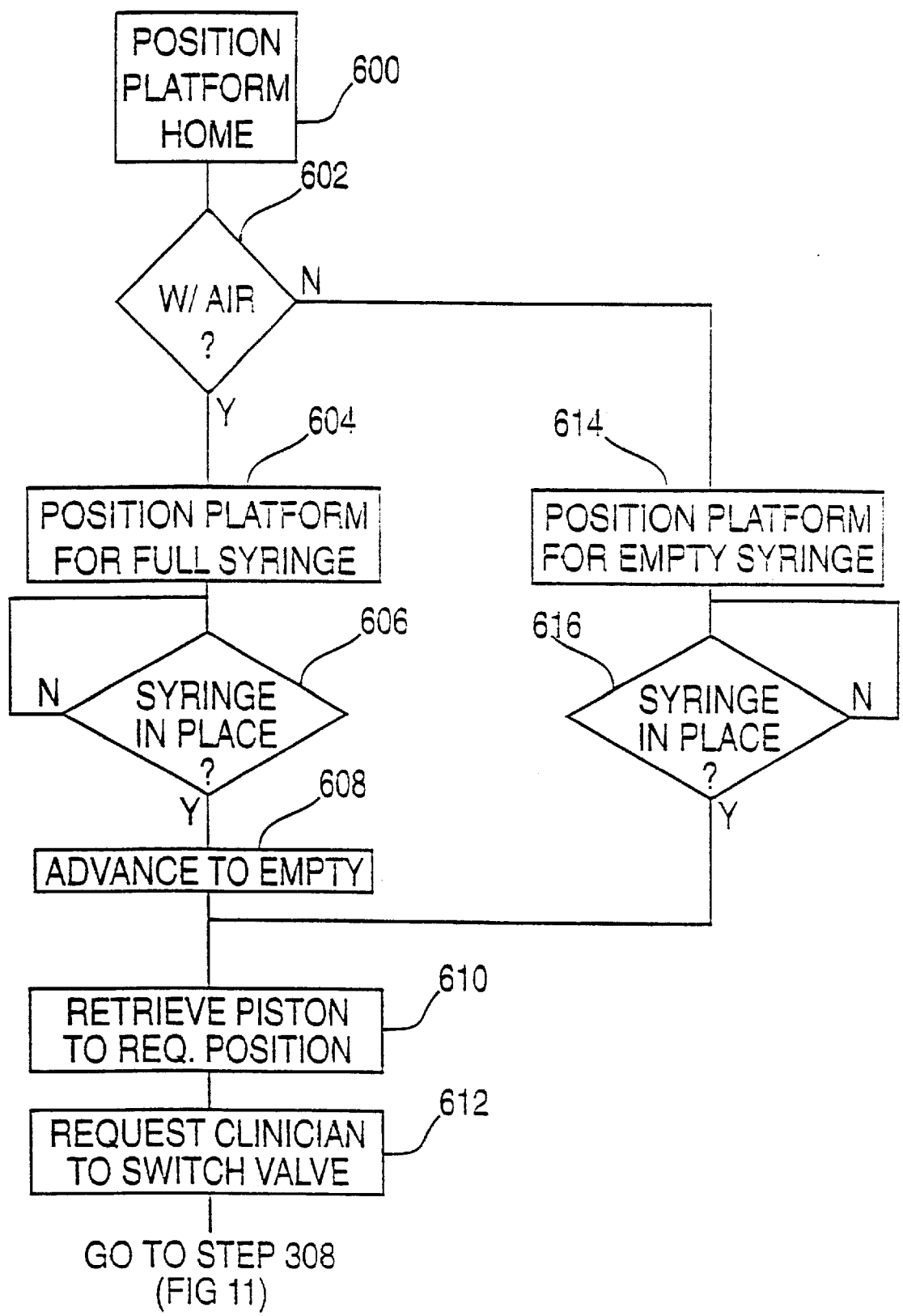
FIG. 18 shows a flow chart for charging a syringe.

Going back to step 302 in FIG. 11, if the device is to be used to charge the syringe, a charging subroutine is initiated, as indicated in FIG. 18. In step 600 of this FIG. the platform 30 is moved to the home position. In step 602 a test is performed to determine if the syringe is to be charged with or without air. If a charging with air is to occur then in step 604 the platform 30 is positioned for the syringe head in the position when the syringe is completely full. In step 606 the system waits for the syringe to be placed.

Figure 19:
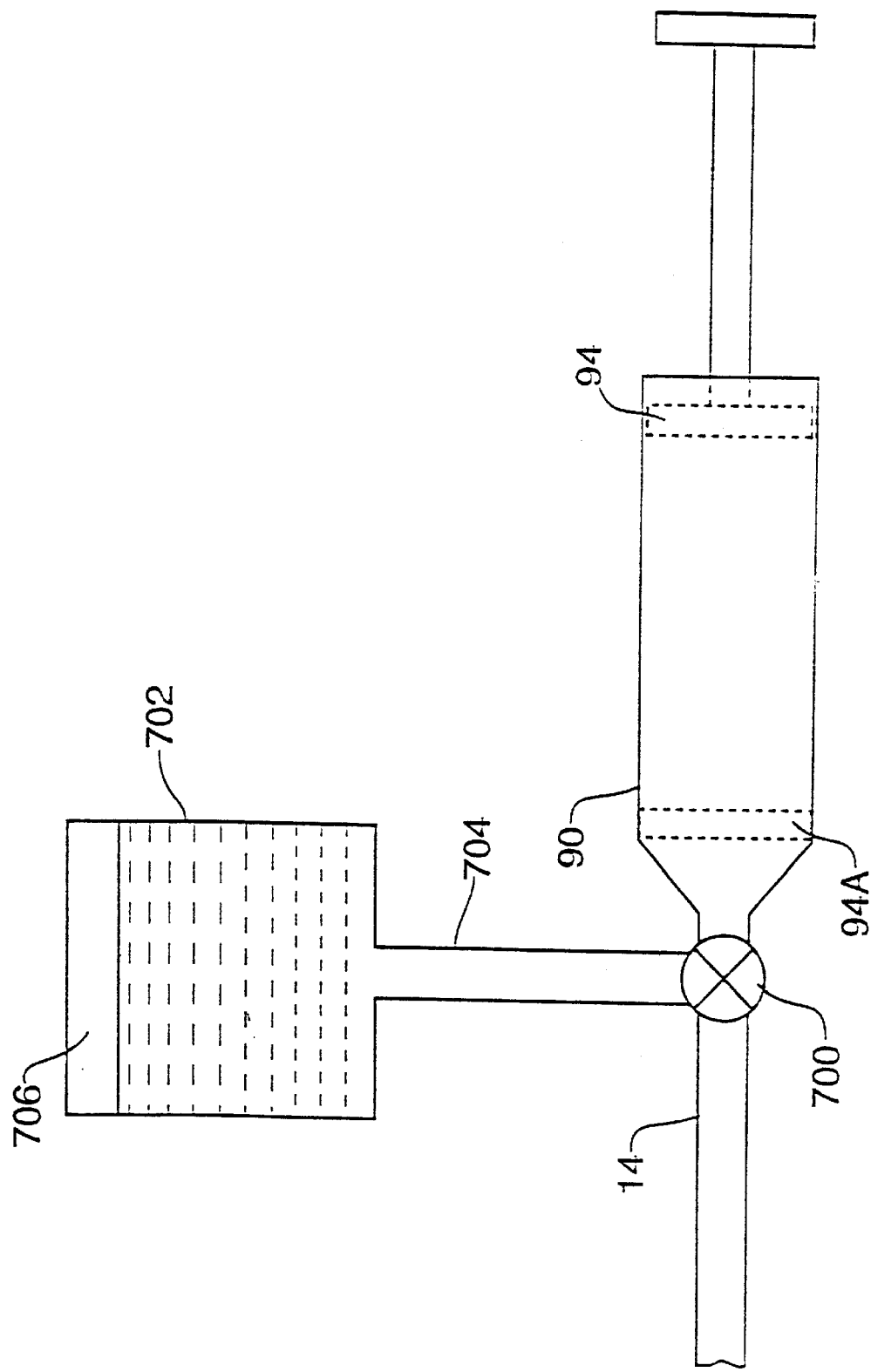
FIG. 19 shows the syringe and associated equipment required for charging.

In order to charge a syringe, the system must be connected to a source of fluid such as a vial or bottle. More particularly, as shown in FIG. 19, in order to achieve charging the syringe 90 is connected to tube 14 through a three-way valve 700. Valve 700 is used to connect the system to fluid source 702 through a pipe 706. For charging the syringe, the valve is positioned so that the fluid source 702 is connected to the syringe. In the FIG. 19, fluid source 702 is shown upside down so that it has an air space 706. For charging with air, the syringe plunger 94 is positioned as if the syringe was full, i.e. in the position shown in FIG. 19. For a charging without air, the syringe plunger is moved in so that it is as close as possible to the opposite end as shown at 94A. Once the connections shown in FIG. 19 are completed, the clinician can position the syringe on the groove 38 and secure it with clamp 40 with the plunger head engaged by platform 30.

Referring back to FIG. 18, in step 606 the syringe is now detected. In step 608 the syringe is advanced to the empty position forcing air from the syringe into the source 702, thereby pressurizing it. In step 610 the position is retrieved to an initial position corresponding to the volume of fluid to be injected as set by the clinician earlier. In step 612 the clinician is reminded to turn the valve 700 to couple the syringe 90 to tube 14. The system now returns to step 308.

If in step 602 it is determined that charging without is to be performed then in step 614 the platform 30 is moved to the empty position of the syringe. The system then waits for the syringe to be placed in its position in step 616, after which the system continues with step 610 as shown.

The system has been described so far as performing an injection process. However, it is obvious to one skilled in the art that it can be used just as effectively to perform a biopsy, for instance to perform a spinal tap, or other similar anaerobic procedures. Essentially the same parameters can be used for this process, with some minor modifications. For instance, instead of defining an exit pressure, the clinician now defines an entry pressure. Some of the subroutines, such as purging, charging or aspiration are not required for biopsy at all.

Obviously numerous modifications may be made to this invention without departing from its scope as defined in the appended claims.

---

PROGRAM LISTING

```
uses math, Sys Utils;
type
T Pressure - Record
    FlowRate: single;        // Cubic Inches/Second (Input)
    MechanismForce: single;  // Pounds (DB)
{MachineResistancd???}
    LoadCellForce: single;   // Pounds (Input)
    SyringeForce: single;    // Pounds (DB)
    SyringeDiameter: single; // Inches (Input)
    SyringeLength: single;   // Inches (DB)
    TubingDiameter: single;  // Inches (DB)
    TubingLength: single;    // Inches (DB)
    NeedleDiameter: single;  // Inches (DB)
    NeedleLength: single;    // Inches (DB)
    SpecificWeight: single;  // Slugs/Cubic Inch (DB)
    Viscosity: single;       // No Units (DB)
The term DB indicates that the value of a parameter is
retrieved from one of the data bases.
    Input - means that the parameter has been calculated
previously
    Calculated - Value calculated by this routine}
end;
The following variables are defined in the course of this
process:
    VelocityLast: single;
    TimeLast: double;
implementation
function CalculatePressure (P:TPressure): single;
const
    KineticEnergyFactor = 2.0;
    Gravity = 386.4;
var
    KineticEnergyFactorSyringe: single;
    KineticEnergyFactorNeedle: single;
```

-continued

PROGRAM LISTING

```
    KineticEnergyFactorTubing: single;
    SyringeFrictionLoss: single;
    SyringeFlowLoss: single;
    SyringeVelocityHead: single;
    NeedleFrictionLoss: single;
    NeedleFlowLoss: single;
    NeedleVelocityHead: single;
    TubingFrictionLoss: single;
    TubingFlowLoss: single;
    VelocityConstant: single;
    StopperForce: single;
    ReynoldsSyringe: single;
    ReynoldsTubing: single;
    ReynoldsNeedle: single;
    NeedlePressure: single; // Value returned
    Volume, Accel: single;
    VelocityNow: single;
    TimeNow: double;
begin
    VelocityConstant :=  P.SpecificWeight /
                         (Sqr(PI / 4.0) * 2.0 * Gravity);
    try
        ReynoldsSyringe := P.Flowrate / (PI * P.SyringeDiameter *
(P.Viscosity / 4));
        if ReynoldsSyringe >= 2000.0 then begin
            KineticEnergyFactorSyringe = 1.0;
            SyringeFrictionLoss :=0.25 / sqr(log10 ( 0.0000012 /
(3.7 * P.SyringeDiameter) +
                         (5.74 / Power(ReynoldsSyringe,
0.9))));
        end else begin
            KineticEnergyFactorSyringe := 2.0;
            SyringeFrictionLoss := (16 * P.Viscosity * PI *
P. SyringeDiameter) /.
                         P.Flowrate
        end;
    except
        SyringeFrictionLoss := 0;
        KineticEnergyFactorSyringe := 0;
    end;
    try
        ReynoldsTubing := P.Flowrate / (PI * P.TubingDiameter *
(P.Viscosity / 4));
        if ReynoldsTubing >= 2000.0 then begin
            KineticEnergyFactorTubing := 1.0;
            TubingFrictionLoss := 0.25 / sgr(log10 ( 0.0000012 /
(3.7 * P.TubingDiameter) +
                         (5.74 / Power(ReynoldsTubing,
0.9))));
        end else begin
            KineticEnergyFactorTubing := 2.0;
            TubingFrictionLoss := (16 * P.Viscosity * PI *
P.TubingDiameter) /
                         P. Flowrate
        end;
    except
        TubingFrictionLoss := 0;
        KineticEnergyFactorTubing := 0;
    end;
    try
        ReynoldsNeedle := P.Flowrate / (PI * P.NeedleDiameter *
(P.Viscosity / 4));
        if ReynoldsNeedle >= 2000.0 then begin
            KineticEnergyFactorNeedle := 1.0;
            NeedleFrictionLoss := 0.25 / sqr(log10 ( 0.0000012 /
(3.7 * P.NeedleDiameter) +
                         (5.74 / Power(ReynoldsNeedle,
0.9))));
        end else begin
            KineticEnergyFactorNeedle := 2.0;
            NeedleFrictionLoss (16 * P.Viscosity * PI *
P.NeedleDiameter) /
                         P. Flowrate
        end;
    except
        NeedleFrictionLoss := 0;
        KineticEnergyFactorNeedle := 0;
```

-continued

PROGRAM LISTING

```
    end;
    Volume :=   ((PI / 4) * sqr(P.SyringeDiameter) *
P.SyringeLength) +
                         ((PI / 4) * sqr(P.TubingDiameter) *
P.TubingLength) +
                         ((PI / 4) * sqr(P.NeedleDiameter) *
P.NeedleLength);
    VelocityNow := P.FlowRate / ((PI / 4) *
Sqr(P.SyringeDiameter));
    TimeNow := flow * 24 * 67 * 60;
    if (TimeLast > 0) and (not P.TestMode) then begin       //
First time entered switch
        Accel := ((P.SpecificWeight * Volume) / Gravity) *
//ABS???
                         ((VelocityLast − VelocityNow) / (TimeNow −
TimeLast))
    end else begin
        Accel := 0;
    end;
    VelocityLast := VelocityNow; // Save for next tme
    TimeLast := TimeNow;
    NeedleVelocityHead := (VelocityConstant *
KineticEnergyFactorNeedle) *
                         (Sqr(P.FlowRate) /
Power(P.NeedleDiameter, 4.0));
    SyringeVelocityHead := (VelocityConstant *
KineticEnergyFactorSyringe) *
                         (Sqr(P.FlowRate) /
Power(P.SyringeDiameter, 4.0));
    SyringeFlowLoss :=  (SyringeFrictionLoss * P.SyringeLength *
Sqr(P.FlowRate)) /
                         (P.SyringeDiameter * 2.0 * Gravity *
                         Sqr(PI * Sqr(P.SyringeDiameter) / 4.0))
;
    TubingFlowLoss :=   (TubingFrictionLoss * P.TubingLength *
Sqr(P.FlowRate)) /
                         (P.TubingDiameter * 2.0 * Gravity *
                         Sqr(PI * Sqr(P.TubingDiameter) / 4.0)) ;
    NeedleFlowLoss :=   (NeedleFrictionLoss * P.NeedleLength *
Sqr(P.FlowRate)) /
                         (P.NeedleDiameter * 2.0 * Gravity *
                         Sqr(PI * Sqr(P.NeedleDiameter) / 4.0))
    StopperForce :=    P.LoadCellForce − P.SyringeForce −
P.MechanismForce;
    //StopperForce :=   P LoadCellForce;
    NeedlePressure :=  (StopperForce / (PI *
sqr(P.SyringeDiameter/2))) −
                         NeedleVelocityHead + SyringeVelocityHead
                         (P. SpecificWeight * (SyringeFlowLoss +
                         TubingFlowLoss + NeedleFlowLoss) −
                         (Accel / (PI * sgr(P.SyringeDiameter /
2))));
end.
```

We claim:

1. An electronic device for selectively injecting or withdrawing fluid from a patient's body comprising:
    a reservoir for injecting or collecting said fluid;
    a fluid delivery system having a first end coupled to said reservoir and a second end adapted to be inserted into the patient's body;
    an electrical drive mechanism arranged and constructed to apply a force within said reservoir in response to commands in one of a first direction in which fluid is injected from said reservoir through said fluid delivery system into the patient and a second direction in which fluid is withdrawn from the patient through said fluid delivery system;
    a sensor coupled to one of said reservoir, fluid delivery system and electrical drive mechanism for sensing an internal parameter indicative of a force generated by said drive mechanism and internal resistances within said reservoir and said fluid delivery system to said force; and a controller coupled to said sensor and said electrical drive mechanism, said controller including a calculator for calculating an entry/exit pressure at said second end as a function of said internal parameter, said controller generating said commands to control said entry/exit pressure.

2. The apparatus of claim 1 further comprising a display coupled to said calculator and adapted to display said exit pressure.

3. The apparatus of claim 1 wherein said sensor is adapted to detect said operational parameter as a function of an internal pressure within said pumping mechanism.

4. The apparatus of claim 1 further comprising a delivery element that delivers said fluid from said pumping mechanism to said patient interface zone, said delivery element presenting a frictional loss to said fluid, said calculator being adapted to determine said exit pressure based on said frictional loss.

5. The device of claim 1 wherein controller generates commands to insure that the entry/exit pressure does not exceed a predetermined threshold, said predetermined threshold is selected to correspond to a pressure level within a patient's tissue which has been determined to minimize pain and/or tissue damage to said patient.

6. An injection device for injection of fluids into body tissues comprising:
a fluid reservoir holding a fluid to be injected;
a fluid delivery section having a first end coupled to said fluid reservoir and a second end adapted to be inserted into the body tissues;
a drive mechanism adapted to generate an internal pressure within said fluid reservoir in response to commands to force said fluid to flow through said fluid delivery section and out through said second end, said fluid having an exit pressure at said second end;
an input element for inputting physical characteristics of at least one of said fluid, said fluid reservoir and said fluid delivery section;
a sensor that senses an internal parameter indicative of said internal pressure; and
a controller receiving said physical characteristics and said internal parameter, said controller including a calculator to determine said exit pressure based on said physical characteristics and said internal parameter, said controller generating said commands to control said exit pressure.

7. An electronic device for selectively injecting or withdrawing fluid from a patient's body comprising:
a reservoir for injecting or collecting said fluid;
a fluid delivery system having a first end coupled to said reservoir and a second end adapted to be inserted into the patient's body;
an electrical drive mechanism arranged and constructed to apply a force within said reservoir in response to commands in one of a first direction in which fluid is injected from said reservoir through said fluid delivery system into the patient and a second direction in which fluid is withdrawn from the patient through said fluid delivery system;
a sensor coupled to one of said reservoir, fluid delivery system and electrical drive mechanism for sensing an internal parameter indicative of a force generated by said drive mechanism;
a controller coupled to said electrical drive mechanism, said controller generating said commands to control the operation of the electrical drive mechanism, and including a calculator calculating an entry/exit pressure at said second end as a function of said internal parameter; and
a speaker generating an audible output indicative of the current value of said entry/exit pressure.

8. The apparatus of claim 7 further comprising a display arranged to display said exit pressure.

9. The apparatus of claim 7 wherein said sensor is adapted to detect a force generated by said pump.

10. The apparatus of claim 7 wherein said sensor is adapted to detect a pressure generated by said pump.

11. The apparatus of claim 7 wherein said delivery system presents a frictional loss to fluid flow and wherein said calculator is adapted to generate said exit pressure based on said frictional loss.

12. The apparatus of claim 7 wherein said delivery system includes a liquid source, a needle and a tube having one end receiving fluid from said source and another end coupled to said syringe, each of said needle and said tube having a specific frictional loss and wherein said calculator is adapted to generate said exit pressure based on said specific frictional losses.

13. The apparatus of claim 12 further comprising a memory adapted to store said specific frictional losses.

14. The apparatus of claim 7 wherein said delivery system presents a frictional loss to fluid flow based on characteristics of said fluid, and wherein said calculator is adapted to generate said exit pressure based on said fluid characteristics.

15. The apparatus of claim 14 wherein said calculator is adapted to generate said exit pressure based on a viscosity of said fluid.

16. The apparatus of claim 14 wherein said calculator is adapted to generate said exit pressure based on a temperature of said fluid.

17. The apparatus of claim 14 wherein said calculator is adapted to generate said exit pressure based on a specific weight of said fluid.

18. The apparatus of claim 14 further comprising a memory adapted to store said fluid characteristic.

19. An electronic injection device for selectively injecting a fluid comprising:
a fluid source adapted to hold said fluid;
a fluid ejection section having a first end coupled to said fluid source and a second end adapted to eject said fluid;
a drive mechanism coupled to said fluid ejection section and arranged and constructed to cause said fluid to be ejected in response to a command signal;
a sensor coupled to said fluid ejection section for sensing an internal pressure of said fluid within said fluid ejection section;
a controller coupled to said drive mechanism, said controller being adapted to generate commands to operate drive mechanism; and
a speaker generating an audible output indicative of the current value of said internal parameter.

20. A method injecting fluids into a body tissue comprising:
providing a reservoir filled with a fluid;
forcing said fluid from said reservoir through a fluid delivery system into the body tissue, said fluid having an exit pressure at an interface between said fluid delivery system and the body tissue;
automatically measuring said exit pressure;
monitoring said exit pressure; and
automatically controlling the flow of said fluid to control said exit pressure.

21. The device of claim 20 wherein said device includes a delivery unit delivering said fluid, said delivery unit exhibiting a frictional loss associated with said fluid, said exit pressure being calculated based on said frictional loss.

22. The device of claim 21 further comprising sensing a fluid velocity within said delivery unit and determining said frictional loss based on said fluid velocity.

23. The device of claim 22 further comprising calculating said fluid velocity based on dimensions of said delivery unit.

24. The device of claim 22 wherein said device includes a memory for storing the dimensions of said delivery unit, further comprising retrieving said dimensions.

* * * * *